US012784191B2

(12) United States Patent
Aykut et al.

(10) Patent No.: US 12,784,191 B2
(45) Date of Patent: Nov. 3, 2026

(54) SYSTEMS, DEVICES, AND METHODS FOR VITAL SIGN MONITORING

(71) Applicant: CareX AI, Inc., Palo Alto, CA (US)

(72) Inventors: Tamay Aykut, Pacifica, CA (US); Hasan Burak Dogaroglu, Munich (DE); Ming-Sung Chao, Munich (DE)

(73) Assignee: CareX AI, Inc., Palo Alto, CA (US)

( * ) Notice: Subject to any disclaimer, the term of this patent is extended or adjusted under 35 U.S.C. 154(b) by 718 days.

(21) Appl. No.: 18/068,463

(22) Filed: Dec. 19, 2022

(65) Prior Publication Data

US 2023/0196567 A1 Jun. 22, 2023

Related U.S. Application Data

(60) Provisional application No. 63/292,165, filed on Dec. 21, 2021.

(51) Int. Cl.
*A61B 5/024* (2006.01)
*G06N 3/0455* (2023.01)
(Continued)

(52) U.S. Cl.
CPC ........ *G06T 7/0012* (2013.01); *A61B 5/02416* (2013.01); *G06N 3/0455* (2023.01);
(Continued)

(58) Field of Classification Search
CPC . A61B 5/0075; A61B 5/0205; A61B 5/02416; A61B 5/14551; A61B 5/7264; G06T 2207/10016; G06T 2207/10024; G06T 2207/20081; G06T 2207/20084; G06T 2207/30076; G06T 2207/30088; G06T 2207/30201; G06T 7/0012;
(Continued)

(56) References Cited

U.S. PATENT DOCUMENTS 10,117,588 B2 11/2018 Lee et al.
10,130,308 B2 * 11/2018 Tzvieli .................. A61B 5/015
(Continued)

FOREIGN PATENT DOCUMENTS

EP 3 749 180 A1 12/2020
WO WO-2021/111436 A1 6/2021
(Continued)

OTHER PUBLICATIONS

Gašper Slapnicar et al.,"Blood Pressure Estimation with a Wristband Optical Sensor," Oct. 8, 2018,UbiComp '18: Proceedings of the 2018 ACM International Joint Conference and 2018 International Symposium on Pervasive and Ubiquitous Computing and Wearable Computers, pp. 758-760.*
(Continued)

*Primary Examiner* — Omar S Ismail
(74) *Attorney, Agent, or Firm* — Cooley LLP

(57) ABSTRACT

Devices, systems, and methods herein relate to non-invasive monitoring of a patient. These systems and methods may receive one or more image signals corresponding to a skin of the patient, process the one or more image signals using a first machine learning model, and predict a physiological parameter based on the processed one or more image signals using a second machine learning model.

47 Claims, 20 Drawing Sheets

(51) Int. Cl.
*G06N 3/0895* (2023.01)
*G06T 7/00* (2017.01)

(52) U.S. Cl.
CPC .. *G06N 3/0895* (2023.01); *G06T 2207/10016* (2013.01); *G06T 2207/30088* (2013.01)

(58) Field of Classification Search
CPC .... G06T 7/0016; G06N 3/045; G06N 3/0455; G06N 3/0895
See application file for complete search history.

(56) References Cited

U.S. PATENT DOCUMENTS

| | | | | |
|---|---|---|---|---|
| 10,376,192 | B2 | 8/2019 | Lee et al. | |
| 10,420,515 | B2 | 9/2019 | Sinha et al. | |
| 10,448,847 | B2 | 10/2019 | Lee et al. | |
| 10,694,988 | B2 | 6/2020 | Lee et al. | |
| 10,702,173 | B2 | 7/2020 | Lee et al. | |
| 10,806,390 | B1 | 10/2020 | Lee et al. | |
| 10,888,256 | B2 | 1/2021 | Lee et al. | |
| 10,905,339 | B2 | 2/2021 | Tsouri | |
| 11,266,356 | B2 | 3/2022 | Sinha et al. | |
| 11,337,626 | B2 | 5/2022 | Lee et al. | |
| 2011/0295515 | A1 | 12/2011 | Grady et al. | |
| 2013/0274610 | A1 | 10/2013 | Kamshilin et al. | |
| 2015/0199010 | A1* | 7/2015 | Coleman | A61B 5/0006 345/156 |
| 2016/0135706 | A1* | 5/2016 | Sullivan | A61B 5/0006 600/509 |
| 2017/0322679 | A1* | 11/2017 | Gordon | G06F 3/013 |
| 2017/0346817 | A1* | 11/2017 | Gordon | G06V 40/10 |
| 2018/0092547 | A1* | 4/2018 | Tzvieli | A61B 5/0075 |
| 2018/0092548 | A1* | 4/2018 | Tzvieli | A61B 5/0013 |
| 2018/0092589 | A1* | 4/2018 | Tzvieli | A61B 5/0075 |
| 2018/0103894 | A1* | 4/2018 | Tzvieli | A61B 5/015 |
| 2018/0103913 | A1* | 4/2018 | Tzvieli | A61B 5/015 |
| 2018/0104439 | A1* | 4/2018 | Tzvieli | A61B 5/015 |
| 2018/0310828 | A1* | 11/2018 | DiMaio | A61B 5/0075 |
| 2019/0026538 | A1* | 1/2019 | Wang | G06V 40/172 |
| 2019/0046044 | A1* | 2/2019 | Tzvieli | A61B 5/0077 |
| 2019/0046099 | A1* | 2/2019 | Lee | A61B 5/0035 |
| 2019/0114824 | A1* | 4/2019 | Martinez | G06N 3/044 |
| 2020/0051217 | A1* | 2/2020 | Shen | G06F 18/214 |
| 2020/0085312 | A1* | 3/2020 | Tzvieli | A61B 5/02055 |
| 2020/0121256 | A1* | 4/2020 | Mcduff | G06N 3/09 |
| 2020/0390337 | A1* | 12/2020 | Frank | A61B 5/0205 |
| 2021/0012769 | A1* | 1/2021 | Vasconcelos | G10L 15/24 |
| 2021/0030289 | A1* | 2/2021 | Ahmed | A61B 5/7257 |
| 2021/0068735 | A1 | 3/2021 | Lee et al. | |
| 2021/0082109 | A1 | 3/2021 | Wu et al. | |
| 2021/0090734 | A1* | 3/2021 | Singh | G06N 3/08 |
| 2021/0113093 | A1 | 4/2021 | Nozawa et al. | |
| 2021/0113105 | A1* | 4/2021 | Wei | A61B 5/02125 |
| 2021/0169400 | A1 | 6/2021 | Fan et al. | |
| 2021/0259557 | A1* | 8/2021 | Frank | A61B 5/0075 |
| 2021/0361208 | A1 | 11/2021 | Lee et al. | |
| 2021/0398337 | A1* | 12/2021 | Mcduff | G06T 13/40 |
| 2021/0407678 | A1* | 12/2021 | Arcot Desai | G06F 8/65 |
| 2022/0007965 | A1* | 1/2022 | Tiron | A61B 5/0823 |
| 2022/0061797 | A1* | 3/2022 | Vernalis | A61B 5/725 |
| 2022/0126864 | A1* | 4/2022 | Moustafa | B60W 60/0013 |
| 2022/0138493 | A1* | 5/2022 | Lee | G06F 18/214 382/103 |
| 2022/0218218 | A1 | 7/2022 | Bao et al. | |
| 2022/0268958 | A1* | 8/2022 | Ahmed | G01V 1/284 |
| 2022/0400943 | A1* | 12/2022 | Lee | A61B 3/024 |
| 2023/0062081 | A1* | 3/2023 | Kuperman | G16H 30/40 |
| 2023/0103762 | A1* | 4/2023 | Alali | E21B 47/00 175/50 |
| 2023/0190140 | A1* | 6/2023 | Tiron | A61B 5/746 600/534 |

FOREIGN PATENT DOCUMENTS

| | | | |
|---|---|---|---|
| WO | WO-2021/149048 | A1 | 7/2021 |
| WO | WO-2025/141420 | A1 | 7/2025 |

OTHER PUBLICATIONS

Dangdang Shao et al. ,"Noncontact Monitoring Breathing Pattern, Exhalation Flow Rate and Pulse Transit Time," Oct. 16, 2014, IEEE Transactions On Biomedical Engineering, vol. 61, No. 11, Nov. 2014, pp. 2760-2765.*

Jiyoung Lee , "Multi-Modal Recurrent Attention Networks for Facial Expression Recognition," Jul. 8, 2020, IEEE Transactions On Image Processing, vol. 29, 2020, pp. 6977-6988.*

Gaper Slapnicar et al., "Blood Pressure Estimation with a Wristband Optical Sensor," Oct. 8, 2018, UbiComp '18: Proceedings of the 2018 ACM International Joint Conference and 2018 International Symposium on Pervasive and Ubiquitous Computing and Wearable Computers, pp. 758-760.*

K. Ashoka Reddy et al., "Motion Artifact Reduction in Photoplethysmographic Signals using Singular Value Decomposition, " Jun. 25, 2007, 2007 IEEE Instrumentation & Measurement Technology Conference IMTC 2007, pp. 1-3.*

Carolin Wuerich et al.,"PTT-based Contact-less Blood Pressure Measurement using an RGB-Camera," Oct. 9, 2021,Current Directions in Biomedical Engineering,vol. 7, Issue 2, pp. 375-377.*

Ramakrishna Mukkamala et al.,"Toward Ubiquitous Blood Pressure Monitoring via Pulse Transit Time: Theory and Practice," Jun. 5, 2015, IEEE Transactions on Biomedical Engineering, vol. 62, No. 8, Aug. 2015,pp. 1879-1892.*

Meng Rong et al.,"A Blood Pressure Prediction Method Based on Imaging Photoplethysmography in combination with Machine Learning," Nov. 21, 2020, Biomedical Signal Processing and Control,vol. 64,Feb. 2021,102328, pp. 1-10.*

Balakrishnan, G. et al. (2013). "Detecting pulse from head motions in video," MIT CSAIL, pp. 3430-3437.

Carni, D.L. et al. (Aug. 8, 2016). "Setting-up of PPG scaling factors for SpO2% evaluation by smartphone," 2016 IEEE International Symposium on Medical Measurements and Applications (MeMeA), Benevento, Italy, May 15-18, 2016, pp. 1-5.

Djeldjli, D. et al. (Feb. 2021). "Remote estimation of pulse wave features related to arterial stiffness and blood pressure using a camera," Biomedical Signal Processing and Control 64:102242, 19 pages.

Di Maria, C. et al. (Jan. 16, 2014). "A pilot study of photoplethysmographic peripheral pulse transit times in paediatric heart transplant recipients and healthy children," Computing in Cardiology 2013, Zaragoza, Spain, pp. 491-494.

Ding, X. et al. (Dec. 17, 2018). "Measuring Oxygen Saturation with Smartphone Cameras Using Convolutional Neural Networks," IEEE Journal of Biomedical and Health Informatics 23(6):2603-2610.

Haque, R. et al. (Feb. 2021). "A Novel Technique for Non-Invasive Measurement of Human Blood Component Levels from Fingertip Video Using DNN Based Models," IEEE Access 9:19025-19042.

He, Q. et al. (Apr. 23, 2021). "Spatiotemporal monitoring of changes in oxy/deoxy-hemoglobin concentration and blood pulsation on human skin using smartphone-enabled remote multispectral photoplethysmography," Biomedical Optics Express 12(5):2919-2937.

He, K. et al. (Dec. 10, 2015). "Deep Residual Learning for Image Recognition," Cornell University, arXiv:1512.03385, located at https://arxiv.org/abs/1512.03385, retrieved on Sep. 11, 2025 (online only), 12 pages.

International Search Report and Written Opinion mailed on Apr. 21, 2025, for PCT Application No. PCT/IB2024/062934, filed on Dec. 20, 2024, 13 pages.

Kim, C-S. et al. (Nov. 2019). "Ballistocardiogram-Based Approach to Cuff-Less Blood Pressure Monitoring: Proof-of-Concept and Potential Challenges," IEEE Trans. Biomed. Eng. 65(11):2384-2391.

Kipf, T. et al. (Feb. 22, 2017). "Semi-Supervised Classification with Graph Convolutional Networks," Cornell University, arXiv:1609.

(56) References Cited

OTHER PUBLICATIONS

02907v4, located at https://arxiv.org/abs/1609.02907v4, retrieved on Sep. 11, 2025 (online only), 14 pages.
Kossack, B. et al. (Sep. 2019). "Local Remote Photoplethysmography Signal Analysis for Application in Presentation Attack Detection," Vision, Modeling, and Visualization VMV2 2019 Conference, Rostock, Germany, pp. 135-142.
Liu, X. et al. (Dec. 24, 2020). "Multispectral Image Reconstruction from Color Images Using Enhanced Variational Autoencoder and Generative Adversarial Network," IEEE Access 9:1666-1679.
Moço, A. et al. (Nov. 2015). "Ballistocardiographic Artifacts in PPG Imaging," IEEE Transactions on Bio-Medical Engineering 63(9):1-8.
Mukkamala, R. et al. (Aug. 1, 2015). "Toward Ubiquitous Blood Pressure Monitoring via Pulse Transit Time: Theory and Practice," IEEE Trans Biomed Eng. 62(8):1879-1901.
Reddy, K.A. et al. (Jun. 25, 2007). "Motion Artifact Reduction in Photoplethysmographic Signals using Singular Value Decomposition," 2007 IEEE Instrumentation & Measurement Technology Conference IMTC 2007, Warsaw, Poland, May 1-3, 2007, pp. 1-4.
Slapničar, G. et al. (Oct. 8, 2018). "Blood Pressure Estimation with a Wristband Optical Sensor," UbiComp '18: Proceedings of the 2018 ACM International Joint Conference and 2018 International Symposium on Pervasive and Ubiquitous Computing and Wearable Computers, pp. 758-761.
Veličković, P. et al. (Feb. 4, 2018). "Graph Attention Networks," Cornell University, arXiv:1710.10903, located at https://arxiv.org/abs/1710.10903, retrieved on Sep. 11, 2025 (online only), 12 pages.
Venkat, S. et al. (Jul. 2019). "Machine Learning based SpO2 Computation Using Reflectance Pulse Oximetry," Annu. Int. Conf. IEEE Eng. Med. Biol. Soc. 2019:482-485.
Wuerich, C. et al. (Oct. 9, 2021). "PTT-based Contact-less Blood Pressure Measurement using an RGB-Camera," Current Directions in Biomedical Engineering 7(2):375-378.

* cited by examiner

1200

Metrics for the respiratory rate prediction algorithms 1420

| Model name | MAE ( BPM ) | SD (BPM) | Accuracy (%) |
|---|---|---|---|
| Model A | 3.82 | 4.20 | 35.59 |
| Model B | 5.23 | 7.60 | 30.52 |
| SSQ Model | **1.18** | **1.44** | **75.19** |

Metrics for the heart rate predictor networks 1430

| Model name | Mean Absolute Error ( BPM ) | Standard Deviation (BPM) |
|---|---|---|
| Model C | 1.38 | 3.44 |
| SSQ Model | **0.95** | **1.64** |

1440

1450

1460

2000

2050

| PPG from RGB reconstruction metrics for the methods | | |
|---|---|---|
| Model name | Pearson Correlation | RMSE |
| CHROM | 0.57 | 0.25 |
| POS | 0.59 | 0.26 |
| AE | **0.68** | **0.19** |
| VQVAE | 0.45 | 0.27 |

2210

2220

SYSTEMS, DEVICES, AND METHODS FOR VITAL SIGN MONITORING

CROSS-REFERENCE TO RELATED APPLICATIONS

This application claims priority to U.S. Provisional Patent Application No. 63/292,165, filed Dec. 21, 2021, the contents of which are incorporated herein by reference.

TECHNICAL FIELD

Devices, systems, and methods herein relate to non-invasive monitoring of a physiological parameter of a patient.

BACKGROUND

Vital signs such as blood pressure and heart rate are commonly used to indicate the status and health of a subject. For example, measurement of blood pressure is commonly performed in a clinical setting using a sphygmomanometer and pressure cuff, which may be cumbersome and impractical for continuous and/or ambulatory blood pressure monitoring. However, vital sign monitoring outside a clinical setting is generally limited due to equipment cost, procedural complexity, and poor patient compliance. As such, additional devices, systems, and methods for physiological parameter estimation may be desirable.

SUMMARY

Described here are patient monitoring devices, systems, and methods for providing real-time, non-invasive monitoring of one or more physiological parameters of a patient, such as vital signs and related metrics. In some variations, a method of monitoring a patient may comprise, at one or more processors, receiving one or more image signals corresponding to a skin of the patient, processing the one or more image signals using a first machine learning model, and predicting a physiological parameter based on the processed one or more image signals using a second machine learning model.

In some variations, the skin corresponds to one or more of a finger and a face of the patient. In some variations, the one or more image signals may be generated by an optical sensor. In some variations, the one or more image signals may comprise a video.

In some variations, processing the one or more image signals may select one or more spatial and temporal portions of the one or more image signals.

In some variations, the first machine learning model may be trained using a first machine learning model training set of photoplethysmography (PPG) signals based on a set of physiological parameter values. In some variations, the set of predetermined physiological parameter values may correspond to one or more of heart rate, heart rate variability, oxygen saturation, respiratory rate, and blood pressure.

In some variations, the first machine learning model training set may comprise PPG signals of a plurality of patients. In some variations, the first machine learning model training set may comprise artificial photoplethysmography PPG signals comprising a set of predetermined physiological parameter values. In some variations, the first machine learning model training set may comprise artificial noise comprising one or more of Gaussian noise, white noise, stretching, sloping, saturation, replacement, scaling, and baseline wander.

In some variations, processing the one or more image signals to select one or more portions of the one or more image signals may be based on one or more of a dominant frequency, maximal variation, a correlation coefficient, contact pressure of a finger to an optical sensor, a cross-correlation among a set of cardiac cycles within a predetermined time period, cycle-by-cycle validation, bandpass filtering, smoothness, motion artifact removal, session filtering, and power spectrum.

In some variations, processing the one or more image signals may comprise modifying the one or more image signals based on a shutter speed and signal gain of an optical sensor associated with the one or more image signals. In some variations, processing the one or more image signals may comprise generating one or more albedo signals corresponding to the one or more image signals. In some variations, the one or more albedo signals may comprise diffuse reflection and may be absent specular reflection.

In some variations, processing the one or more image signals comprises selecting a face and a neck of the skin of the one or more image signals, and extracting a mean RGB signal of the selected skin as input to the first machine learning model. In some variations, extracting the mean RGB signal may comprise applying z-normalization separately to a plurality of sliding windows of the mean RGB signal, wherein the z-normalization comprises per temporal point normalization with respect to a local neighborhood. In some variations, the first machine learning model training set may be trained with a self-supervised learning mean RGB training set comprising artificial noise comprising one or more of Gaussian noise, Gaussian blur, cropping, and cutout.

In some variations, the first machine learning model may comprise one or more of a residual neural network (ResNet), U-Net, variational autoencoder, denoising autoencoder neural network, autoencoder neural network with residual connections, vector quantized autoencoder, graph convolutional network, graph attention network, multi-head attention transformer, U-Net model, and combinations thereof.

In some variations, the first and second machine learning models may comprise one or more of self-supervised learning, semi-supervised learning, weakly-supervised learning, and federated learning. In some variations, processing the one or more image signals may comprise generating a polygon mesh corresponding to a face and neck of the patient.

In some variations, processing the one or more image signals may comprise generating a virtual multispectral PPG signal.

In some variations, processing the one or more image signals may comprise applying one or more of a Kalman filter, principal component analysis, independent component analysis, and blind source separation.

In some variations, the physiological parameter may comprise one or more of oxygen saturation and blood glucose. In some variations, the second machine learning model may comprise one or more of a long short-term memory network (LSTM), a bi-directional long short-term memory network (bi-LSTM), convolutional neural network (CNN), deep neural network, a gradient boosting model, transformers, and combinations thereof.

In some variations, the physiological parameter may comprise blood pressure. In some variations, the second machine learning model may comprise one or more of a Bayesian network, a long short-term memory network (LSTM), a bi-directional long short-term memory network (bi-LSTM), a convolutional neural network (CNN), a random forest, a gradient boosting model, a Wave net model, a residual neural network (ResNet) model, a WaveResNet model, a support vector machine (SVM), autoencoder, and combinations thereof.

In some variations, predicting the physiological parameter may comprise calculating one or more of a short time Fourier transform (STFT), a continuous wavelet transform (CWT), a synchro-squeezing transform (SSQ), and a PPGlet of the processed one or more image signals as input to the second machine learning model. In some variations, predicting the physiological parameter may comprise calculating for the processed one or more image signals one or more of systolic amplitude, pulse area, pulse interval, heart rate, time between systolic peak and end of a cardiac cycle, ratio of time before and after a systolic peak in a cardiac cycle, pulse width, maximum upslope, absorbance, Kaiser-Teager energy, signal energy, magnitude, phase, crest time, pulse interval, pulse width at half height (PWHH), Dicrotic Notch time ($T_n$), A2 time (A2T), diastolic time (DT), first derivative peak time (FDPT), pulse area (PA), area 1, area 2, pulse height (PH), ratio of b peak to a peak of a second derivative (b/a), ratio of e peak to a peak of the second derivative (e/a), modified Normalized Pulse Volume (mNPV), mean arterial pressure (MAP), cardiac output (CO), and total peripheral resistance (TPR).

In some variations, the blood pressure may comprise a continuous arterial blood pressure. In some variations, predicting the physiological parameter may comprise calculating for the processed one or more image signals an upper envelope corresponding to systolic blood pressure and a lower envelope corresponding to diastolic blood pressure.

In some variations, predicting the blood pressure may comprise calculating for the processed one or more image signals one or more of a pulse transit time (PTT) based on a plurality of portions of the face of the patient, a PTT between the face and the finger, and a modified Normalized Pulse Volume (mNPV) and a photoplethysmography (PPG) signal based on the finger or the face.

In some variations, the physiological parameter may comprise respiratory rate. In some variations, predicting the physiological parameter may comprise calculating a synchro-squeezing transform (SSQ) of the processed one or more image signals as input to the second machine learning model. In some variations, predicting the physiological parameter may comprise cropping a respiratory rate frequency region. In some variations, the second machine learning model may comprise a U-Net neural network. In some variations, processing the one or more image signals may comprise extracting one or more of frequency modulation, amplitude modulation, and baseline wander of one or more color channels of the PPG signal.

In some variations, the physiological parameter may comprise heart rate. In some variations, predicting the physiological parameter may comprise calculating a synchro-squeezing transform (SSQ) of the processed one or more image signals as input to the second machine learning model. In some variations, predicting the physiological parameter may comprise one or more of cropping a heart rate frequency region, beat detection, peak detection, and combinations thereof.

In some variations, the physiological parameter may comprise heart rate variability. In some variations, the heart rate variability may comprise one or more of a standard deviation of NN intervals (SDNN), a mean of the NN (e.g., peak-to-peak distance) intervals, and a root mean square of successive differences between normal heartbeats (RMSSD). In some variations, predicting the physiological parameter may comprise extracting color channels from the processed one or more image signals and identifying a set of peak locations.

Also described herein are methods of monitoring a physiological parameter of a patient using a finger of the patient. In some variations, a method of monitoring a patient may comprise, at one or more processors, receiving one or more image signals corresponding to a finger of the patient, selecting one or more spatial and temporal portions of the one or more image signals based on contact pressure of the finger to an optical sensor, and predicting a physiological parameter based on the selected one or more spatial and temporal portions using a machine learning model.

Also described herein are methods of monitoring a physiological parameter of a patient using a face. In some variations, a method of monitoring a patient may comprise, at one or more processors, receiving one or more image signals corresponding to a face of the patient, processing the one or more image based on a shutter speed and signal gain of an optical sensor associated with the one or more image signals, and predicting a physiological parameter based on the processed one or more image signals using a machine learning model.

Also described herein are methods of monitoring blood pressure of a patient using a finger and face. In some variations, a method of monitoring a patient may comprise, at one or more processors, receiving one or more image signals corresponding to a finger and face of the patient, processing the one or more image signals using a first machine learning model, predicting blood pressure based on the processed one or more image signals using a second machine learning model.

Also described herein are methods of monitoring a cough of a patient. In some variations, a method of monitoring a patient may comprise, at one or more processors, receiving an audio signal of the patient, processing the audio signal using a first machine learning model trained using an augmented training set, and classifying a cough parameter based on the processed audio signal using a second machine learning model.

In some variations, processing the audio signal may select one or more portions of the audio signal. In some variations, the augmented training set may comprise artificial noise comprising one or more of Gaussian noise, white noise, frequency mask, time mask, pitch change, time shift, and time stretch. In some variations, the first machine learning model may comprise supervised learning.

In some variations, processing the one or more audio signals may comprise extracting a mel spectrogram from the audio signal. In some variations, the first machine learning model may comprise one or more of a residual neural network (ResNet), a convolutional neural network, a hybrid binary and multiclass classification model, and combinations thereof. In some variations, the cough parameter may comprise one or more of cough, non-cough, dry cough, and wet cough.

Also described here are systems. In some variations, a system may comprise an optical sensor configured to generate one or more image signals corresponding to a skin of the patient, a memory, and a processor operatively coupled to the memory and the optical sensor. The processor may be configured to receive one or more image signals corresponding to a skin of the patient using the optical sensor, process the one or more image signals using a first machine learning model, and predict a physiological parameter based on the processed one or more image signals using a second machine learning model.

In some variations, the system may comprise a pressure sensor configured to measure finger pressure against the optical sensor. In some variations, the system may comprise an audio sensor configured to measure patient audio. In some variations, the system may comprise a handheld housing. Processing the one or more image signals and predicting the physiological parameter may be performed within the handheld housing.

In some variations, the system may comprise a communication device and a display operatively coupled to the processor. The processor may be configured to establish a video conference using the communication device, and output the predicted physiological parameter using the display during the video conference.

In some variations, the system may comprise a communication device operatively coupled to the processor, the processor configured to transmit the predicted physiological parameter to a predetermined device using the communication device.

DETAILED DESCRIPTION

Figure 1:
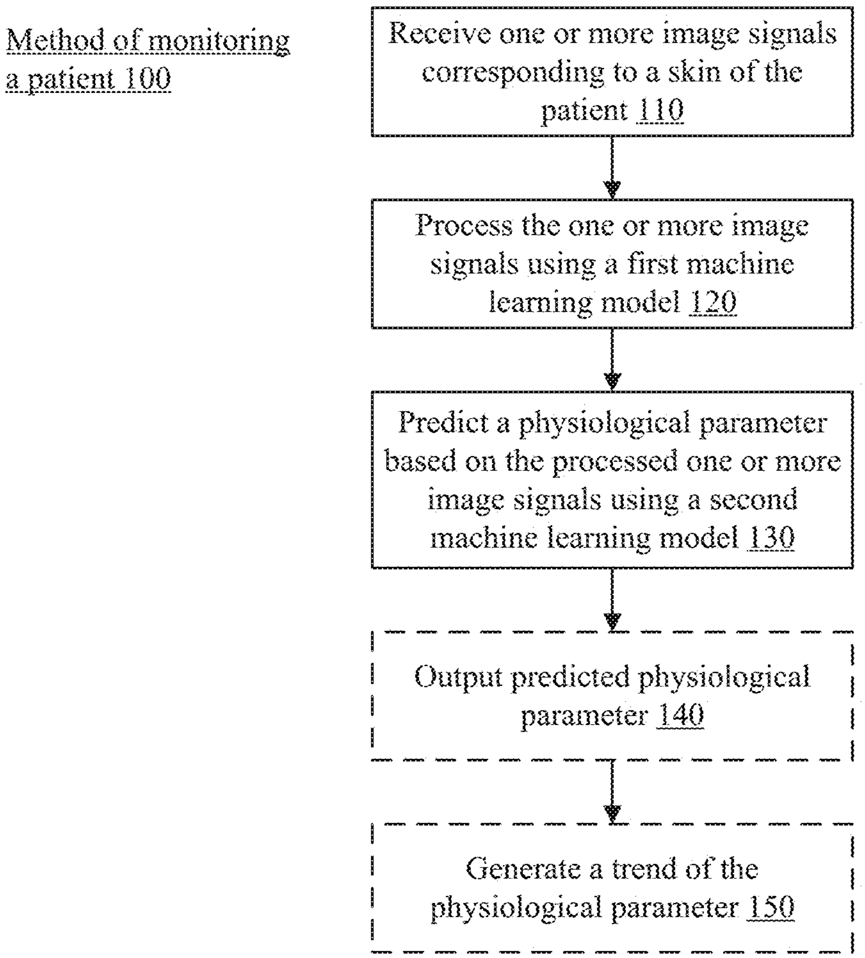
FIG. 1 is a flowchart of an illustrative variation of a method of monitoring a physiological parameter of a patient.

Described here are systems, devices, and methods for non-invasively monitoring a physiological parameter (e.g., characteristic, biomarker) of a patient, such as a vital sign or related metric. These systems, devices, and methods may receive and process patient data (e.g., image data, audio data) using one or more signal processing, image processing, computer vision, and machine learning (e.g., deep learning, reinforcement learning) techniques for predicting one or more physiological parameters (e.g., vital signs). One or more of the physiological parameters may be predicted using, for example, a machine learning model with medical-grade accuracy using commonly available hardware.

In some variations, patient data may be monitored non-invasively using a computing device such as a smartphone, tablet, portable computer, and the like. For example, a smartphone camera may be used to record image data corresponding to one or more of a finger and a face of the patient for processing and vital sign prediction. This may, for example, allow insight into a set of vital signs of a patient on a continuous or semi-continuous, real-time basis. Furthermore, the physiological parameter predictions may be generated securely without patient-identifiable information (e.g., does not include the recorded image data of a face), thereby enhancing the privacy of patient data. For example, the patient data may be processed in a computationally efficient manner such that older and/or less capable hardware (e.g., processor, camera) may be utilized (e.g., without processing using a communication channel and a remote server), thereby increasing adoption among patients otherwise hindered by financial, geographic, cultural, and/or structural barriers. About one in five Americans (e.g., about 60 million people) live in rural areas that traditionally face access challenges to hospital-level care. Thus, the devices described herein for use in predicting a physiological parameter may be portable and utilize existing hardware such that they may allow for continuous or semi-continuous, real-time monitoring with intuitive operation by the patient. Improved monitoring and patient compliance may lead to earlier and/or predictive diagnosis, preventative care, and treatment that improve patient outcomes.

By contrast, conventional methods of determining blood pressure often require use of, for example, a blood pressure cuff and a stethoscope, that can be cumbersome, and difficult to use outside of a clinical setting for a non-medical professional. These conventional methods also fail to provide continuous or semi-continuous monitoring and require training. The systems, devices, and methods described herein are advantageous relative to conventional methods in several ways. For example, the devices, systems, and methods, are intuitive for a non-medical professional to use, and provide an efficient and portable way to predict and monitor health indicators over time. Moreover, the devices, systems, and methods may be configured for a wide range of hardware specifications and environmental conditions (e.g., lighting conditions).

In some variations, a physiological parameter (e.g., vital sign) may comprise one or more of a heart rate, heart rate variability, respiratory rate, oxygen saturation, blood pressure, blood glucose, and voice (e.g., cough). As used herein, patient data may refer to one or more image signals and audio signals measured over a predetermined time period.

I. Methods

Also described here are methods for non-invasively monitoring a physiological parameter (e.g., characteristic) of a patient using the systems and devices described herein. In particular, the systems, devices, and methods described herein may be used to accurately predict and monitor values of a physiological parameter, such as, for example, heart rate, heart rate variability, respiratory rate, oxygen saturation, blood pressure, blood glucose, and voice (e.g., cough). The predicted physiological parameter may be used in a variety of ways. For example, as will be described herein, the physiological parameter may be output (e.g., displayed) to one or more of a patient and health care professional on a computing device and/or may be stored on the computing device or on a server for later viewing on the computing device. For example, the predicted physiological parameter may be estimated and displayed in real-time during a telehealth meeting (e.g., video conference) between the patient and their health care professional. That is, one or more of the image data and the audio data of the patient may be simultaneously used for estimating a set of patient vital signs for display on a video conference. For example, as described in more detail with respect to FIGS. 6-9, the estimated vital signs may be displayed in real-time. The methods described herein may promote the use of telehealth visits by facilitating high-quality care while reducing the risk of disease transmission (e.g., COVID-19) that may occur during in-person visits. Additionally or alternatively, the patient may self-monitor themselves independently of a meeting or videoconference with a health care professional. For example, the patient may track a set of their vital signs on a predetermined schedule (e.g., daily before breakfast).

In some variations, the values of the predicted physiological parameter may be used to establish trends for clinical assessments of the patient. Additionally or alternatively, in some variations, the physiological parameters may be utilized to remotely monitor and/or manage a user. For example, users with known risk factors may be more actively and comprehensively monitored using an application. Health care providers, for example, primary care physicians and/or specialists, may use the information to prescribe a medication regimen and/or to inform therapy decision-making.

In some instances, the predicted physiological parameter may be used in conjunction with data from other devices or applications (e.g., an activity or fitness tracker, a sleep tracker, a glucometer, an internet-enabled scale and/or body composition device, a meditation tracker) to provide a patient or a health care professional with a more comprehensive view of the patient's health. In some variations, the predicted physiological parameter may be exported to or used by applications or devices that may analyze them in conjunction with other health related data (e.g., activity data, fitness data, sleep data, weight, body fat percentage, temperature, blood glucose, or the like).

Overview

In some variations, clinical insights into patient health may be derived using a computing device having a sensor including one or more of an optical sensor, microphone, and/or pressure sensor. For example, a smartphone camera may be configured to generate patient image data for vital sign prediction using one or more signal processing and explainable machine learning models. The prediction may be performed by the computing device for remote patient monitoring and/or telehealth applications. It should be appreciated that any of systems and devices described herein may be used in any of the methods described here.

FIG. 1 is a flowchart depicting an illustrative variation of a method of monitoring a patient (100). In the variation depicted in FIG. 1, the method (100) may comprise receiving one or more image signals corresponding to a skin of the patient (110). In some variations, the skin corresponds to one or more of a finger and a face of the patient, and/or any portion of the body having a sufficient blood vessel structure beneath the skin that may be sufficiently imaged. For example, the image signal may comprise a face and a portion of the patient's body, and any corresponding background (e.g., FIG. 9). In some variations, one or more of the image signals may be generated by an optical sensor. As used herein, image signal may refer to a single image or a plurality of images (e.g., video). For example, one or more of the image signals may comprise a video having a predetermined duration (e.g., about 8 seconds).

Signal Processing

The received image signals may be processed to improve the image signal for physiological parameter prediction by, for example, removing extraneous features (e.g., patient body, background objects, overexposure, strong illumination). Signal processing as described herein may enable lower quality data to be used for parameter prediction while maintaining or improving accuracy. In some variations, one or more of the image signals may be processed using a first machine learning model (120). Additionally or alternatively, one or more of the image signals may be processed using one or more signal processing techniques, as described in more detail herein. In some variations, the received signal may comprise one or more of an image signal (e.g., video), audio signal (e.g., voice), and a user input (e.g., keyboard input, touchscreen input).

Generally, photoplethysmography (PPG) is the optical measurement of a change in light absorption corresponding to a change in blood volume associated with heart contraction. When the heart pumps blood, the arteries distend to accommodate the new volume of blood. This increased blood volume increases the amount of light absorbed by the blood, which can be measured by an optical sensor (e.g., photodetector, camera).

In some variations, processing one or more of the image signals selects one or more spatial and temporal portions of the one or more image signals. For example, portions of an image signal that do not contain a finger or a face may be identified and removed to reduce computational load and/or increase prediction accuracy. In some variations, one or more spatial and temporal portions of the one or more image signals may be selected based on one or more validation parameters comprising one or more of a dominant frequency, maximal variation, a correlation coefficient, contact pressure of a finger to an optical sensor, a quality index, a cross-correlation among a set of cardiac cycles within a predetermined time period, cycle-by-cycle validation, band-pass filtering, smoothness, motion artifact removal, session filtering, and power spectrum. The validation parameters may be computed for a plurality of temporal portions (e.g., window) of a signal. A temporal portion may comprise a plurality of cardiac cycles.

In some variations, a dominant frequency may comprise a peak frequency in a frequency domain representation of the received image signals (e.g., peak frequency of a power spectral density of a signal generated by a fast Fourier transform (FFT)). In some variations, an image signal window may be discarded if a dominant frequency is not within a predetermined range of a predetermined heart rate label. In some variations, maximal recent variations correspond to a maximal intensity change of the image signals in a predetermined time period. In some variations, a correlation coefficient between a red image signal and a blue image signal may correspond to a Pearson correlation coefficient between a red signal window and a blue signal window. In some variations, contact pressure may correspond to a pressure applied by a finger to an optical sensor when an image signal is being generated.

In some variations, a quality index may comprise a ratio of a sum of power spectrum components in a narrow band of a fundamental (e.g., dominant) frequency ($f_c$) and a second harmonic ($2f_c$), and a sum of all the components not previously considered and greater than about 0.5 Hz. In some variations, the quality index may be computed by multiplying the image signal by a hamming window and calculating a power spectrum (e.g., using a FFT) with a resolution of about 0.01 Hz). If the fundamental frequency ($f_c$) is outside the range of about 0.5 Hz to about 3 Hz (e.g., about 30 bpm to about 180 bpm) or if a second tone with the highest power is outside the range of about $0.9f_c$ to about $1.1f_c$, then the quality index may be zero. Image signals with a quality index below about 2 may be discarded. If the frequency requirements are fulfilled, then the quality index is calculated as a sum of the power spectrum components in a range between about $0.9f_c$ and about $2f_c$ divided by the sum of the power spectrum components outside of this range.

In some variations, a cross-correlation (e.g., Pearson correlation coefficient) among a set of cardiac cycles within a predetermined time period (e.g., among cardiac cycles within an image signal window) may be calculated where a mean of the correlations of the cardiac cycles correspond to the cardiac cycles correlation of that window.

In some variations, one or more spatial and temporal portions of the one or more image signals may be selected based on one or more cycle-by-cycle validation, adaptive bandpass filtering, singular value decomposition, session filtering (e.g., session-wise elimination), and peak/valley detection. In some variations, cycle-by-cycle validation may comprise selecting individual cardiac cycles within an image signal window based on a direct linear correlation between the cardiac cycle and a reference cardiac cycle using the Pearson correlation coefficient and resampling the cycles to the same length before calculating the correlation with the reference cardiac cycle. In some variations, the reference cardiac cycle is a mean of all the cardiac cycles within an image signal window. In some variations, adaptive bandpass filtering comprises applying a passband filter having a range based on a fundamental frequency of the image signal. In some variations, one or more motion artifacts of an image signal may be removed using singular value decomposition.

In some variations, session filtering comprises removing sessions where a predetermined number of image signal windows have already been removed. For example, if a session has lost a predetermined percentage (e.g., 90%) of the windows within the image signal window, then the entire image signal window (e.g., session) may be removed (e.g., eliminated).

In some variations, peaks/valley detection may comprise removing a peak in a first or last cycle of an image signal window. For example, a dynamic range of an image signal window may be obtained. A prominence of the peaks may be calculated based on a prominence ratio (e.g., about 0.2) times the dynamic range. The peaks satisfying the prominence may be identified. Valleys may be defined as a minimum point between consecutive peaks, a minimum point between a start of an image signal window and the first peak, or a minimum point between the last peak and a last cycle of the image signal window.

In some variations, processing the received image signals may comprise extracting one or more color channel (e.g., red, blue) features from an image signal. The image signal may be processed based on the extracted features. For example, the extracted color channel feature may comprise one or more of a baseline of a red channel of an image signal window ($DC_{red}$), a baseline of a blue channel of an image signal window ($DC_{blue}$), an amplitude variation of a red channel of an image signal window ($AC_{red}$), an amplitude variation of a blue channel of an image signal window ($AC_{blue}$), a ratio ($R_{red}$) of the AC to DC of the red channel ($AC_{red}/DC_{red}$), a ratio ($R_{blue}$) of the AC to DC of the blue channel ($AC_{blue}/DC_{blue}$), a ratio ($R_{AC}$) of ($AC_{red}$) to ($AC_{blue}$), a ratio ($R_{DC}$) of ($DC_{red}$) to ($DC_{blue}$), and a ratio-of-ratios (R) defined by $(AC_{red}/DC_{red})/(AC_{blue}/DC_{blue})$. In some variations, the ratio-of-ratios R and $R_{DC}$ may be normalized and the ratio-of-ratios R and $R_{DC}$ may be normalized by a min-max normalization (scaled R, scaled $R_{DC}$).

In some variations, the quality of a physiological parameter prediction may be improved by considering the optical sensor settings and compensating as appropriate. In some variations, a received image signal may be processed based on optical sensor settings such as shutter speed and signal gain (e.g., ISO). For example, processing one or more of the image signals may comprise modifying one or more of the image signals based on a shutter speed and signal gain of an optical sensor associated with the one or more image signals. In some variations, the image signal may be processed based on equation 1:

$$PPG^{o} = \left[\frac{PPG - DC(SS_{ori}, ISO_{ori})}{AC(SS_{ori}, ISO_{ori})}\right] \times AC(SS_{ref}, ISO_{ref}) + DC(SS_{ref}, ISO_{ref}) \quad \text{(eqn. 1)}$$

In equation 1, $PPG_C$ is the optical sensor calibrated image signal, PPG is the received image signal, DC is a baseline of the image signal, AC is an amplitude variation of the image signal, $SS_{ori}$ is a shutter speed corresponding to the received image signal, $SS_{ref}$ is a shutter speed of a reference setting, $ISO_{ori}$ is the signal gain corresponding to the received image signal, and $ISO_{ref}$ is the signal gain corresponding to a reference setting.

In some variations, a virtual multispectral PPG signal may be generated from an RGB image signal that is a PPG signal at a plurality of spectral wavelengths. In some variations, processing one or more of the image signals comprises generating a virtual multispectral PPG signal using one or more of a variational autoencoder and a transformation matrix. FIG. 10C is a schematic diagram of a variational autoencoder (1060). In some variations, a virtual multispectral PPG signal may be generated using a transformation matrix as shown in equation 2:

$$\begin{bmatrix} M_1(x, y) \\ M_2(x, y) \\ \vdots \\ M_n(x, y) \end{bmatrix} = W \times \begin{bmatrix} R(x, y) \\ G(x, y) \\ B(x, y) \end{bmatrix}, \quad \text{(eqn. 2)}$$

In equation 2, n is the number of multispectral images, W is the transformation matrix, $M_i$ is the ith multispectral image, (R, G, B) are the RGB images, and (x, y) are the positions of the pixels in an image.

In some variations, processing one or more of the image signals comprises applying one or more of a Kalman filter, principal component analysis, independent component analysis (ICA), and blind source separation. In some variations, processing one or more of the image signals uses a plurality of processing techniques. An output of the plurality of processing techniques may be merged.

In some variations, processing one or more of the image signals for blood pressure estimation may comprise receiving an image signal having a sampling frequency of about 30 Hz and image signal windows of about 8 seconds and a stride of about 2 seconds. The image signal may be filtered using a zero-phase Butterworth filter of order 4 from about 0.5 Hz to about 4 Hz. Baseline wander may be removed and the image signal may be processed based on a quality index as described in more detail herein. In some variations, the image signal may be re-scaled to a range between −1 and 1. Peaks and valleys may be identified for cardiac cycle determination. Cycle-by-cycle validation may be performed to select a set of valleys. One or more features (e.g., systolic amplitude, pulse area, pulse interval, etc.) may be extracted from the processed image signal and averaged for each respective image signal window, as described in more detail herein. One or more of the extracted features may be selected based on a Pearson correlation coefficient. For example, if the Pearson correlation coefficient is greater than about 0.7 for a pair of features, then one of the features may be discarded.

Machine Learning Model

In some variations, an image signal may be processed using a first machine learning model to improve (e.g., denoise) the image signal for physiological parameter prediction. For example, the first machine learning model may comprise one or more of a residual neural network (ResNet), variational autoencoder, denoising autoencoder neural network, autoencoder neural network with residual connections, vector quantized autoencoder, graph convolutional network, graph attention network, multi-head attention transformer, and combinations thereof. The output of the first machine learning model may be a denoised image signal. For example, a WaveResNet model may be configured to denoise a fingertip image signal.

In some variations, the denoising autoencoder neural network may be U-net-based (e.g., BuriGNet) comprising a three-layer convolutional neural network that receives inputs of shape (N, 1, 240) where N is the batch size. An initial layer may have a larger kernel (e.g., size 11) than the kernel (e.g., size 3) of subsequent layers in order to cover different types of noise. For similar reasons, a dilation of the first layer may be 1 while a dilation of the second and third layers may be 2. In some variations, an image signal of a predetermined length (e.g., about 8 seconds) may be resampled at about 30 Hz and min-max normalized. In some variations, the three channels may have 32, 64, and 128 filters, respectively. In some variations, an activation function, batch norm, and max pool downsampling may be applied to each layer. In some variations, at the end of the encoder, the model may be configured to output a latent representation of (N, 128, 30). In some variations, the decoder may be a mirror image of the encoder. That is, the decoder may comprise the same layer parameters in the reverse order while replacing one-dimensional convolutions with one-dimensional transposed convolutions such that each next layer is double the size of the previous layer. The output of the decoder may be a tensor of shape (N, 1, 240) at the end that represents the denoised versions of the input signals. In some variations, a predictor may be a parallel branch with a long short-term memory (LSTM) layer with about 30 timesteps, about 128 encoding dimensions, and about a 32 hidden size followed by a simple linear layer to convert the LSTM layer's output to a scalar representing the physiological parameter (e.g., heart rate). In some variations, nonlinearities between the layers of the denoising autoencoder may be rectified linear units except for the output of the predictor where a sigmoid function may be applied to squeeze the predicted scalar between zero and one.

In some variations, the denoising autoencoder neural network may be a Bayesian iteration of a BuriGNet (e.g., variational BuriGNet or VBuriGNet) configured to output an uncertainty of predictions. In some variations, network weights may be sampled where the same input may be run through a network a plurality of times in order to measure certain/uncertain regions of the image signal. In some variations, the uncertainty measurement may be used to mark certain portions of an image signal as certain (e.g., clean, trusted) or uncertain.

Machine Learning Model Training

In some variations, the machine learning model may be trained using an augmented data set comprising artificial noise and/or artificial PPG signals to construct a set of PPG signals with predetermined or random parameters values based on real and/or artificial PPG signals. For example, the first machine learning model may be trained using a first machine learning model training set of photoplethysmography (PPG) signals comprising a set of physiological parameter values. Furthermore, the first machine learning model training set may comprise artificial photoplethysmography PPG signals comprising a set of predetermined physiological parameter values. In some variations, the set of predetermined physiological parameter values may correspond to one or more of heart rate, heart rate variability, oxygen saturation, respiratory rate, and blood pressure. In some variations, the first machine learning model training set may comprise PPG signals of a plurality of patients.

In some variations, artificial noise may be added to a PPG signal (e.g., artificial or real) to simulate realistic image signals to better train the first machine learning model. In some variations, the first machine learning model training set may comprise artificial noise comprising one or more of Gaussian noise, white noise, stretching, sloping, saturation, replacement, scaling, and baseline wander. White noise may comprise an additive noise sampled from a Gaussian distribution with zero mean. Stretching may comprise a portion of an image signal that is stretched through time and added back to the original image signal to simulate an echo. Sloping may comprise a linearly increasing or decreasing portion of the image signal added to the original image signal. Cutout may comprise a portion of the image signal replaced with a random constant to simulate no data reading situations. Saturation may comprise one or more portions of an image signal replaced with a maximum or minimum possible value to account for sensor limitations. Scaling may comprise a portion of the image signal replaced with a scaled up or down version of itself to simulate momentary sensor calibration. Baseline wander may comprise a very low frequency noise with a random phase added to the image signal to represent movement and filtering side effects.

In some variations, a plurality of augmented image signals may be generated from a single image signal using a mean RGB augmentation. In some variations, the first machine learning model training set may comprise a self-supervised learning mean RGB training set comprising artificial noise comprising one or more of Gaussian noise, Gaussian blur, cropping, and cutout. In some variations, the first and second machine learning models may comprise one or more of self-supervised learning, semi-supervised learning, weakly-supervised learning, and federated learning.

Figure 10B:
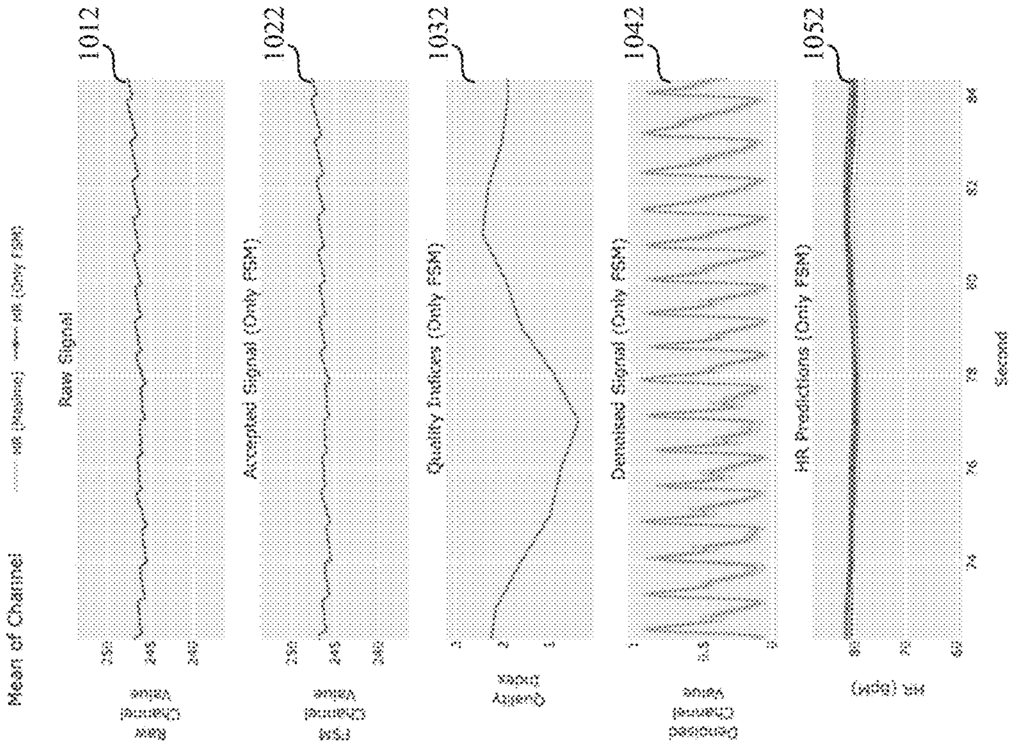
FIGS. 10A and 10B are illustrative variations of vital sign signal processing.
Figure 10A:
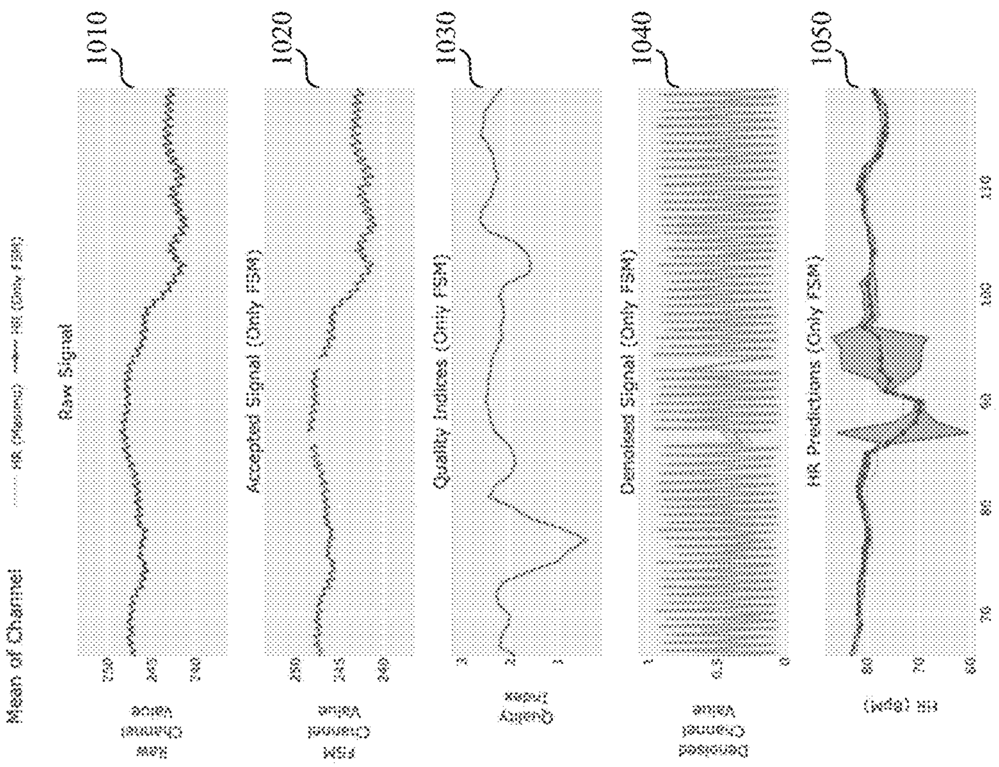
Figure 10C:
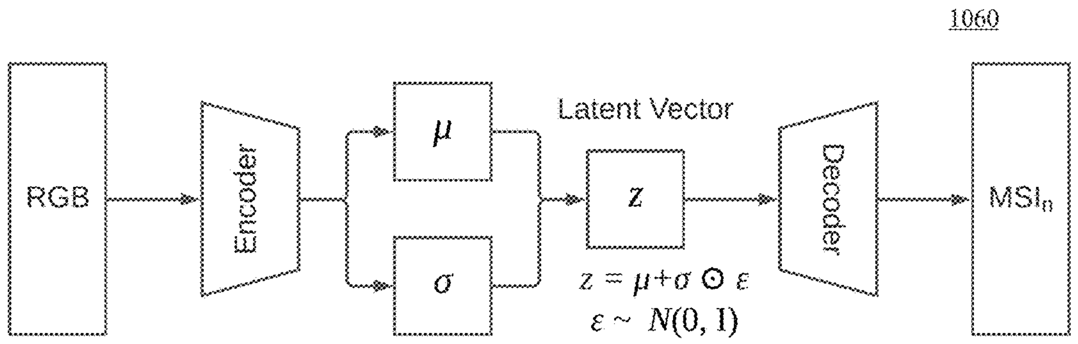
FIG. 10C is a block diagram of an illustrative variation of a variational autoencoder.

FIGS. 10A and 10B are illustrative variations of image signal processing of patient data. FIG. 10B depicts a specific portion of the image signal shown in FIG. 10A. The image signal generated by an optical sensor may be measured as a raw signal (1010, 1012). In some variations, the raw signal (1010, 1012) may be pre-processed (e.g., using a finite state machine (FSM)) to generate a pre-processed signal (1020, 1022) that may remove one or more portions of the raw signal (1010, 1012) as described in more detail herein. In some variations, a quality index (1030, 1032) of the pre-processed signal (1020, 1022) may be calculated for further signal processing. In some variations, the pre-processed signal (1020, 1022) may be further processed to generate a processed (e.g., denoised) signal (1040, 1042) based at least on the quality index (1030, 1032) as described in more detail with respect to signal processing. In some variations, the processed signal (1040, 1042) may be used to predict a physiological parameter such as heart rate (HR) (1050, 1052) as described in more detail with respect to parameter prediction.

Parameter Prediction

As shown in method (100) of FIG. 1, one or more physiological parameters (e.g., vital signs) may be predicted based on the processed one or more image signals using a second machine learning model (130).

i. Oxygen Saturation ($SpO_2$) and Blood Glucose

In some variations, the physiological parameter to be predicted may be one or more of oxygen saturation and blood glucose. In some of these variations, the second machine learning model used to predict oxygen saturation and/or blood glucose may comprise one or more of a long short-term memory network (LSTM), a bi-directional long short-term memory network (bi-LSTM), a convolutional neural network (CNN), a deep neural network, a gradient boosting model, a transformer, and combinations thereof.

Figure 11A:
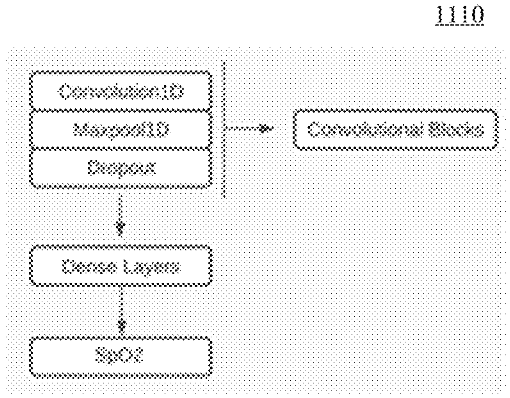
FIG. 11A is a block diagram of an illustrative variation of a convolutional neural network model.
Figure 11B:
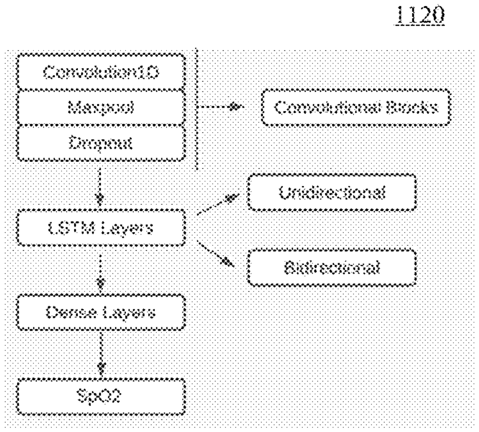
FIG. 11B is a block diagram of an illustrative variation of a convolutional long short-term memory neural network model.
Figure 11C:
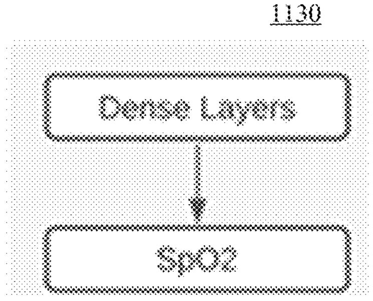
FIG. 11C is a block diagram of an illustrative variation of a deep neural network model.
Figure 11D:
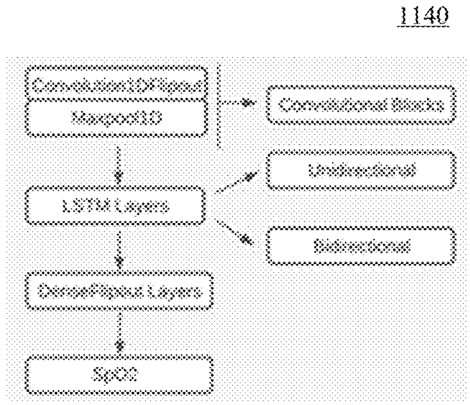
FIG. 11D is a block diagram of an illustrative variation of a Bayesian convolutional long short-term memory neural network model.

For example, FIG. 11A is a block diagram of a convolutional neural network (CNN) model (1110) comprising convolutional blocks, dense layers, and a lambda layer. FIG. 11B is a block diagram of a convolutional long short-term memory neural network (CNN+LSTM) model (1120) comprising convolutional blocks, LSTM layers, dense layers, and a lambda layer. In some variations, a double step CNN model may be used where a parameter (e.g., oxygen saturation, blood glucose) prediction for a first image signal window output from a CNN+LSTM model may be used as an input feature for prediction for a second image signal window. In some variations, an overlapping windows CNN model may be used where the prediction comprises a mean of a set of consecutive image signal window predictions. FIG. 11C is a block diagram of a deep neural network model (1130) comprising dense layers and a lambda layer. FIG. 11D is a block diagram of a Bayesian convolutional long short-term memory neural network (Bayesian CNN+LSTM) model (1140) comprising convolutional blocks, Dense-Flipout layers, and a lambda layer. For each of the neural network models illustrated and described herein, different combinations and numbers of blocks and layers may be used.

In some variations, a first machine learning model may comprise a two state XGBoost regressor where a prediction from a first XGBoost Regressor model is input to a second XGBoost regressor model. In some of these variations, the input to the second XGBoost regressor model may comprise one or more of a mean of the previous three image signal windows, only the last image signal window, and a trend of the previous three image signal windows.

In some variations, a first machine learning model may comprise a Bayesian XGBoost regressor where a predetermined number of predictions (e.g., 50 predictions) may be generated by a random set of iteration ranges. The prediction may correspond to a mean of the predictions and a standard deviation may comprise a range of the predictions.

ii. Blood Pressure

In some variations, the physiological parameter to be predicted may be blood pressure. In some of these variations, the second machine learning model used to predict blood pressure may comprise one or more of a Bayesian network, a long short-term memory network (LSTM), a bi-directional long short-term memory network (bi-LSTM), a convolutional neural network (CNN), a random forest, a gradient boosting model, a Wave net, a residual neural network (ResNet), a support vector machine (SVM), auto-encoder, and combinations thereof.

In some variations, the second machine learning model may be a Bayesian iteration of a BuriGNet (e.g., variational BuriGNet). For example, a VBuriGNet encoder may encode and concatenate the image signal with one or more extracted features of the image signal. The encoded image signal may be input to an LSTM-based network to predict systolic and diastolic blood pressure.

In some variations, the second machine learning model may comprise a WaveResNet model passing an output to a U-net model comprising a predetermined number of levels (e.g., about 5) and configured to reconstruct an envelope of a continuous arterial blood pressure signal from the received image signal. In some variations, one or more features extracted from a fingertip image signal may be concatenated for each of the WaveResNet and U-net model.

In some variations, the trained WaveResNet model may be used to train the U-net model with residual connections where the U-net model receives the reconstructed envelope from the WaveResNet model, adds the fingertip image signal as a second channel, and iteratively refines the envelope prediction. The iterative outputs may be fed as input back to the U-net model as a second channel alongside the image signal. The output of the U-net model may correspond to arterial blood pressure, which may be processed to generate a set of systolic and diastolic blood pressure predictions.

In some variations, the second machine learning model may be a random forest (RF) configured to receive the image signal and a set of extracted features of the image signal comprising one or more of mean peak interval, mean peak-to-valley distance, mean peak amplitude, mean pulse area, mean pulse interval, mean time peak-to-end, mean pulse width, mean max upslope, and mean diastolic amplitude. In some variations, the set of extracted features may be concatenated with one or more patient features (e.g., age, weight, height, etc.).

In some variations, the second machine learning model may comprise an XGBoost model configured to receive the image signal and a set of extracted features of the image signal comprising one or more of mean peak interval, mean peak-to-valley distance, mean peak amplitude, mean pulse area, mean pulse interval, mean time peak-to-end, mean pulse width, mean max upslope, and mean diastolic amplitude. In some variations, the set of extracted features may be concatenated with one or more patient features (e.g., age, weight, height, etc.).

In some variations, predicting the physiological parameter may comprise calculating one or more of a short time Fourier transform (STFT), continuous wavelet transform (CWT), and PPGlet (as described in more detail herein) of the processed one or more image signals as input to the second machine learning model.

In some variations, the second machine learning model may comprise a ResNet model receiving as input a short time Fourier transform (STFT), synchro-squeezing transform (SSQ), or continuous wavelet transform (CWT) representation of the image signal. The output of the model predicts a range-normalized ground truth blood pressure for the given time period. In some variations, the STFT, SSQ, or CWT of the image signal may be calculated for a predetermined image signal window (e.g., about 30 seconds).

In some variations, the second machine learning model may comprise a SSQ-UNet model receiving as input a STFT or CWT representation of the image signal. The output of the model predicts a ground truth blood pressure for the given time period. In some variations, the STFT or CWT of the image signal may be calculated for a predetermined image signal window (e.g., about 30 seconds).

Figure 12:
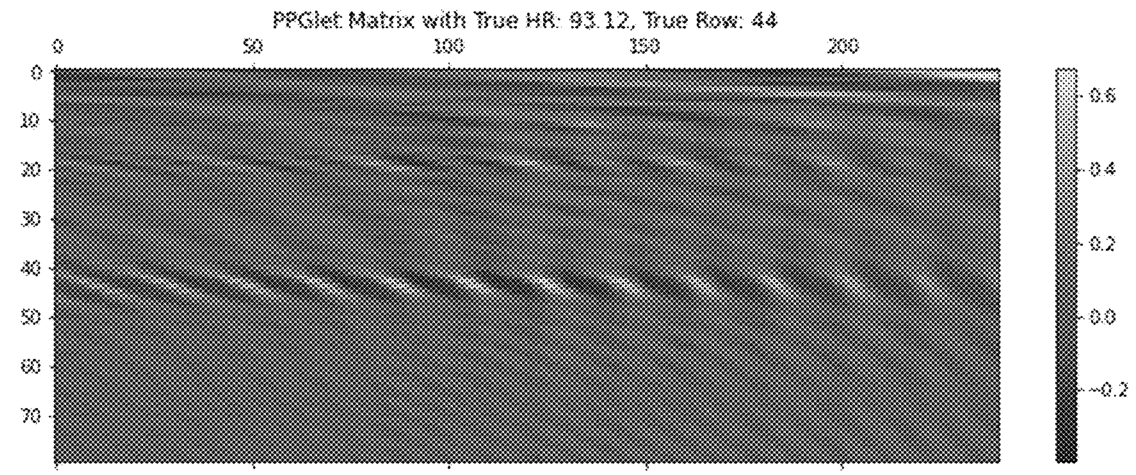
FIG. 12 is a plot of an illustrative variation of a PPGlet output matrix.

In some variations, a PPGlet comprises a wavelet having a shape of a PPG beat (e.g., ideal PPG beat, patient PPG beat) applied to a received image signal and processed to predict a heart rate of the patient. In some variations, a continuous wavelet transform having a predetermined frequency range is applied to the received image signal to generate a matrix (1200) of frequency and timesteps as shown in FIG. 12. The elements of the matrix (1200) correspond to an instantaneous correlation of the PPGlet to a corresponding image signal at a predetermined time step. The matrix may be processed to predict one or more of a heart rate or respiratory rate.

In some variations, predicting the physiological parameter may comprise calculating for the processed one or more image signals one or more of systolic amplitude, pulse area, pulse interval, heart rate, time between systolic peak and end of a cardiac cycle, ratio of time before and after a systolic peak in a cardiac cycle, pulse width, maximum upslope, absorbance, Kaiser-Teager energy, signal energy, magnitude, phase, crest time, pulse interval, pulse width at half height (PWHH), Dicrotic Notch time ($T_n$), A2 time (A2T), diastolic time (DT), first derivative peak time (FDPT), pulse area (PA), area 1, area 2, pulse height (PH), ratio of b peak to a peak of a second derivative (b/a), ratio of e peak to a peak of the second derivative (e/a), modified Normalized Pulse Volume (mNPV), mean arterial pressure (MAP), cardiac output (CO), and total peripheral resistance (TPR).

Systolic amplitude (SA) may comprise an amplitude of the systolic peak. Pulse area (PA) may comprise a total area under a PPG curve. Pulse interval (PI) may comprise a distance between a beginning and an end of the image signal waveform. Pulse width (PW) may comprise an elapsed time between sampling points at about 0.25, about 0.5 and about 0.75 of the height of a systolic peak. Max upslope (MU) may comprise a highest value of the first derivative of the image signal. Absorbance may comprise a minus logarithm of a ratio of incident and outgoing light intensities which may be represented by a peak and valley of the image signal. KTE (Kaiser-Teager Energy) may comprise an instantaneous energy of a PPG signal.

In some variations, the blood pressure may comprise arterial blood pressure. In some variations, predicting the physiological parameter may comprise calculating for the processed one or more image signals an upper envelope corresponding to systolic blood pressure and a lower envelope corresponding to diastolic blood pressure.

iii. Respiratory Rate

Figure 14A:
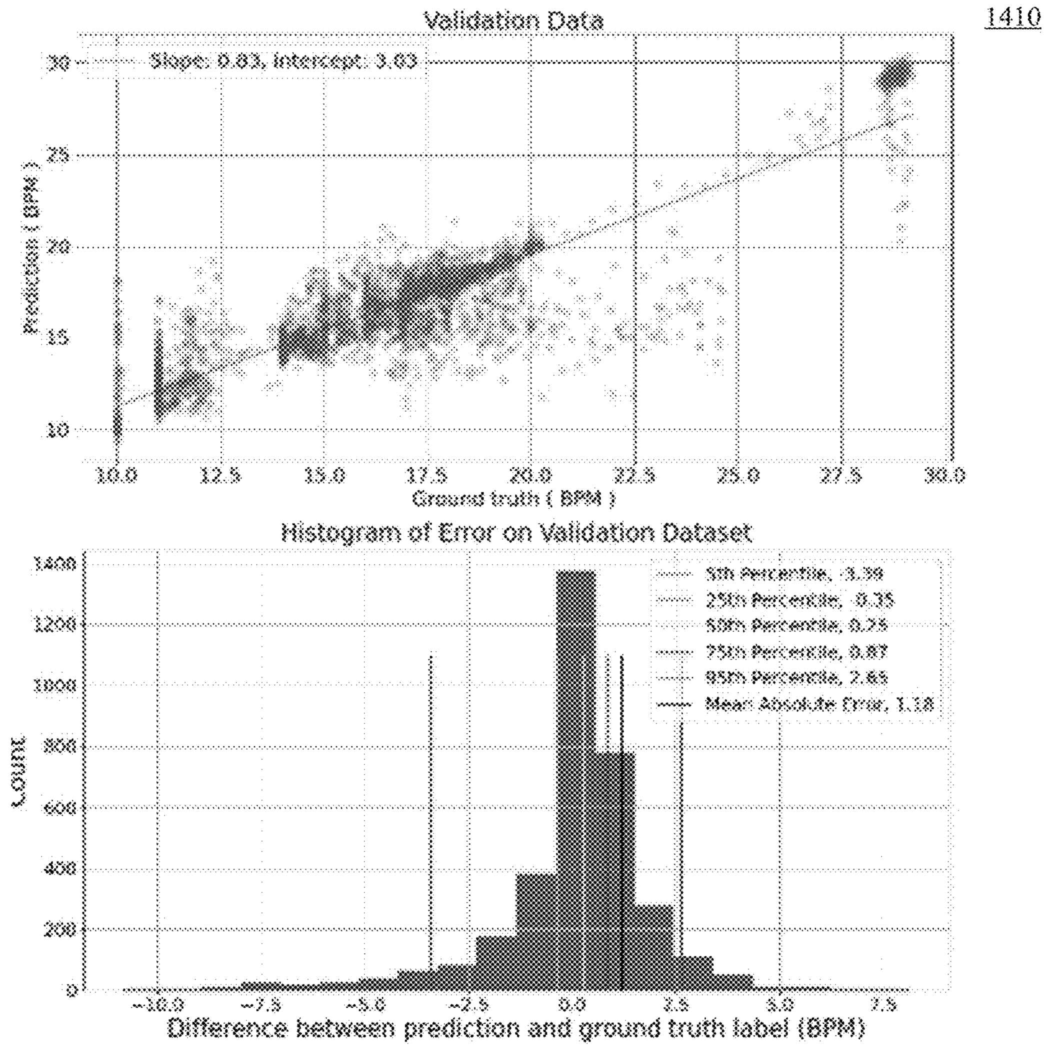
FIG. 14A are plots of an illustrative variation of respiratory rate prediction error and heart rate prediction error.

In some variations, the physiological parameter to be predicted may be a respiratory rate. In some of these variations, predicting the physiological parameter such as respiratory rate comprises calculating a synchro-squeezing transform (SSQ) of the processed one or more image signals as input to the second machine learning model. In some variations, the second machine learning model may comprise an SSQ-UNet model receiving as input a cropped respiratory rate frequency region of the image signal and the model outputs a respiratory rate prediction. FIG. 14A includes a set of error plots (1410) and a table (1420) of the predicted respiratory rate error based on the SSQ-UNet model and alternative respiratory rate models A, B, and C.

Figure 13:
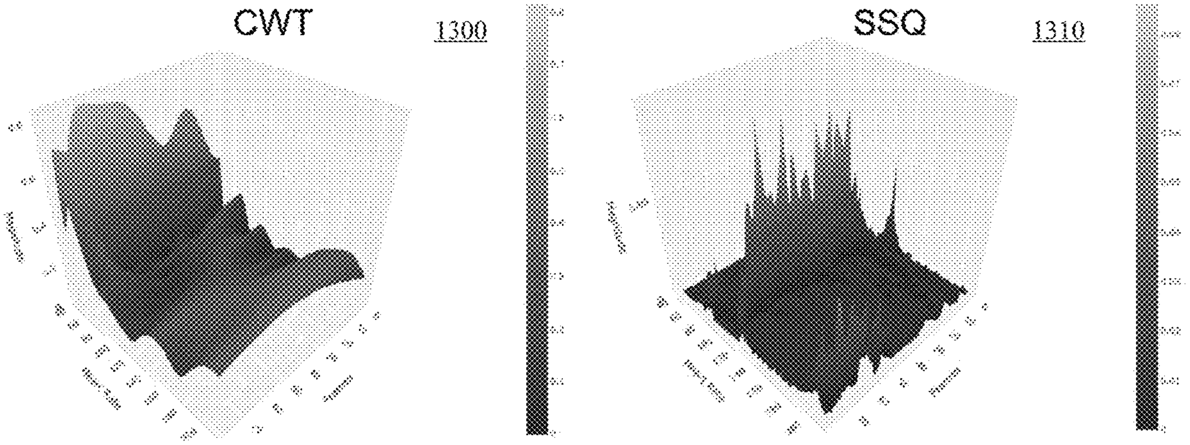
FIG. 13 are plots of an illustrative variation of a continuous wavelet transform and a synchro-squeezing transform.

As shown in FIG. 13, a synchro-squeezing transform (1310) is a version of a continuous wavelet transform (1300) where energy diffusion is condensed into a sparse representation using instantaneous frequency, which may reduce computational load. In some variations, the SSQ-UNet model may receive as input a portion (e.g., patch) extracted from a SSQ of a PPG signal. In some variations, the SSQ-UNet model comprises a two-dimensional U-Net model having an output that is fed into a first and second parallel processing path. In the first processing path, a series of two-dimensional convolutional layers reduce the U-Net model output's dimensionality and flattens into a temporal-frequency vector. In the second processing path, the mean of each row of the U-Net output forms an average energy vector. The first and second processing paths converge where the end, two paths converge both vectors into a single output vector. In some variations, the output vector may be processed using two fully connected layers to generate a physiological parameter prediction (e.g., respiratory rate, heart rate).

Additionally or alternatively, processing one or more of the image signals may comprise extracting one or more of frequency modulation, amplitude modulation, and baseline wander of one or more color channels of the PPG signal. In some variations, one or more of the frequency modulation and amplitude modulation may be input to the second machine learning model to predict a physiological parameter (e.g., respiratory rate, heart rate).

iv. Heart Rate

In some variations, the physiological parameter may comprise a heart rate. In some variations, predicting the physiological parameter (e.g., heart rate) may comprise calculating a synchro-squeezing transform (SSQ) of the processed one or more image signals as input to the second machine learning model. In some variations, predicting the physiological parameter may comprise one or more of cropping a heart rate frequency region, beat detection, peak detection, and combinations thereof.

In some variations, predicting the physiological parameter may comprise calculating a synchro-squeezing transform (SSQ) of the processed one or more image signals as input to the second machine learning model. In some variations, the second machine learning model may comprise a SSQ-UNet model (similar to that described with respect to FIG. 13) receiving as input a cropped heart rate frequency region of the image signal to output a heart rate prediction. The output of the model predicts a ground truth heart rate for the given time period. As shown in table (1430) of FIG. 14A, the predicted heart rate of an illustrative SSQ-Unet model has a mean absolute error (MAE) of 0.95 beats per minute (BPM) and a standard deviation of 1.64 for the SSQ-UNet model.

Prediction Output

Optionally, the predicted physiological parameter may be output (140). For example, the output may be Bayesian and comprise a distribution of outputs for the prediction. In some variations, the predictions may be generated and output in real-time on one or more computing devices. This may be useful in, for example, a telehealth visit between a patient and their health care professional. Additionally or alternatively, the predicted physiological parameter may be stored in memory.

Figure 6:
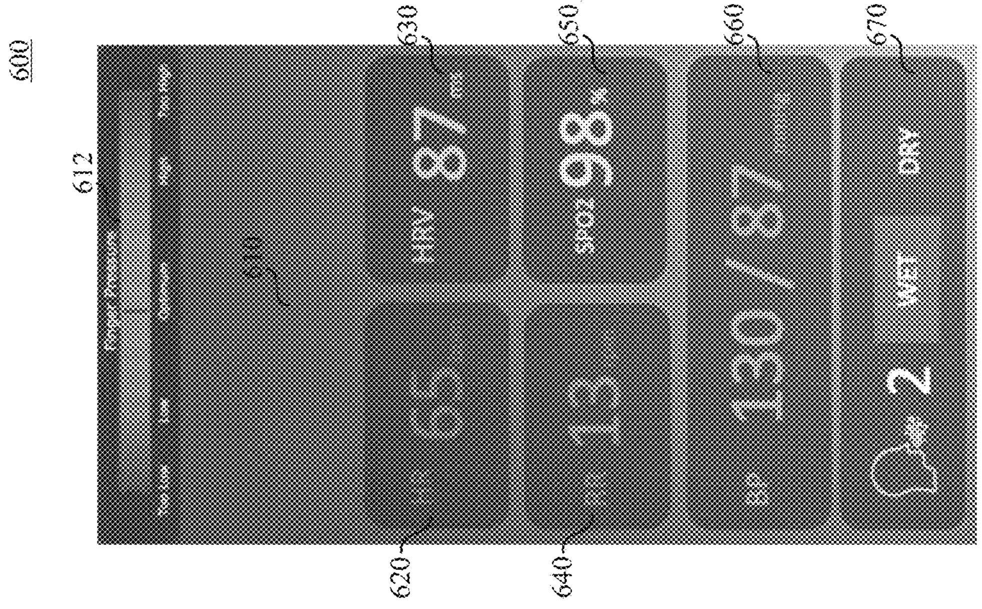
FIG. 6 is another illustrative variation of a graphical user interface relating to patient monitoring using a finger.

FIGS. 6-9 illustrate variations of graphical user interfaces comprising real-time physiological parameter predictions. FIG. 6 depicts a graphical user interface (GUI) (600) relating to patient monitoring using image data of a finger of a patient. In some variations, the patient may be instructed to place their finger over an optical sensor so as to cover a smartphone camera (e.g., front-facing camera, rear-facing camera). In some variations, an illumination source (e.g., flashlight) of a computing device (e.g., smartphone) may be configured to illuminate the patient (e.g., finger, face) based on light conditions. In some variations, the GUI (600) may comprise an optical sensor display region (610) configured to output the image signal (e.g., video) recorded by the optical sensor in real-time. In some variations, the GUI (600) may comprise one or more physiological parameter predictions (620, 630, 640, 650, 660, 670). For example, the predictions may be overlaid above the optical sensor display region (610). As shown in FIG. 6, the GUI (600) may include, but is not limited to, a heart rate display region (620), a heart rate variability display region (630), a respiratory rate display region (640), an oxygen saturation display region (650), a blood pressure display region (660), and a cough display region (670). Furthermore, any of the GUIs described herein may include a glucose display region (not shown). In some variations, the physiological parameter predictions may be output in the GUI (600) using one or more alphanumeric characters, symbols, colors, image, and graphics. For example, a patient's oxygen saturation level may be output as a percentage value in the oxygen saturation display region (650) with color coding (e.g., green, yellow, red) indicating corresponding health status.

In some variations, a contact pressure display region (612) may be configured to guide the patient to apply finger pressure against the optical sensor within a predetermined range. For example, the contact pressure display region (612) may output measured contact pressure against the optical sensor relative to a predetermined scale (e.g., too low, low, optimum, high, too high) in real-time.

Additionally or alternatively, a contact pressure and/or a predicted physiological parameter may be communicated using a set of light patterns. The light patterns described herein may, for example, comprise one or more of flashing light, occulting light, isophase light, etc., and/or light of any suitable light/dark pattern. Light pulse patterns may include one or more colors (e.g., different color output per pulse), light intensities, and frequencies. Additionally or alternatively, a measured contact pressure may be output using respective audio and haptic devices. For example, a speaker of a computing device may audibly beep when the finger pressure applied to the optical sensor is within a predetermined optimal range of contact pressure. A haptic motor of the computing device may vibrate when the finger pressure applied to the optical sensor is outside the predetermined optimal range. Contact pressure measurements outside the predetermined range may include noise that reduce the accuracy of a physiological parameter prediction. In some variations, a physiological parameter prediction may be performed only when the measured contact pressure against the optical sensor is within a predetermined range. Additionally or alternatively, one or more of the predicted physiological parameters may be output using respective audio and haptic devices.

Figure 7:
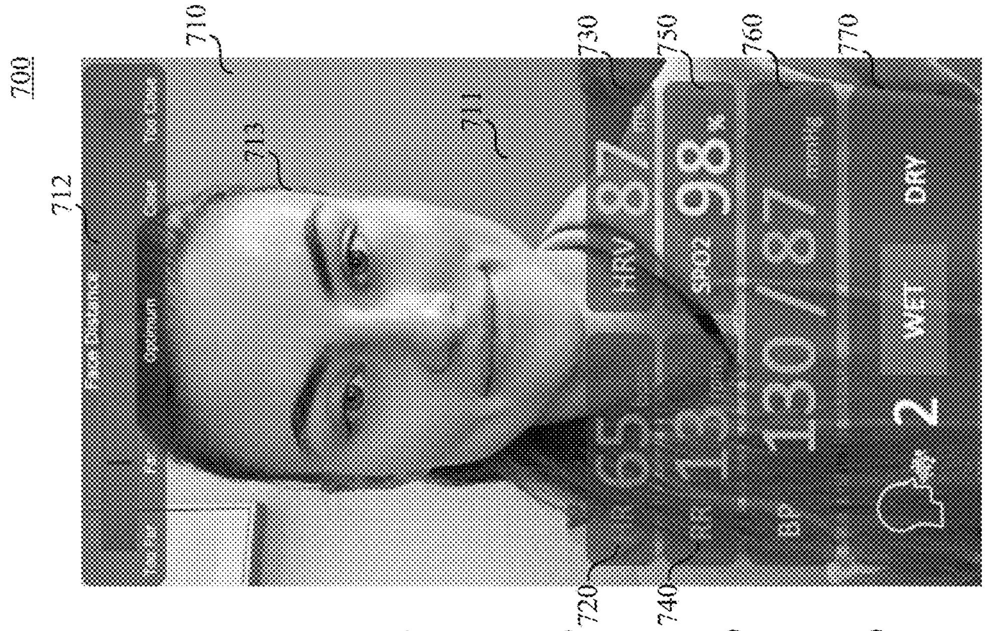
FIG. 7 is an illustrative variation of a graphical user interface relating to patient monitoring using a face.

FIG. 7 depicts a graphical user interface (700) relating to patient monitoring using a face of a patient. In some variations, the patient may be instructed to position their face within range of an optical sensor such as a smartphone camera, web cam, and the like. In some variations, the GUI (700) may comprise an optical sensor display region (710) configured to output the image signal (e.g., video) recorded by the optical sensor in real-time. In some variations, the GUI (700) may comprise one or more physiological parameter predictions (720, 730, 740, 750, 760, 770). For example, the predictions may be overlaid above the optical sensor display region (710). As shown in FIG. 7, the GUI (700) may comprise a heart rate display region (720), a heart rate variability display region (730), a respiratory rate display region (740), an oxygen saturation display region (750), a blood pressure display region (760), and a cough display region (770). In some variations, the physiological parameter predictions may be output in the GUI (700) using one or more alphanumeric characters, symbols, colors, image, and graphics in a similar manner as described with respect to GUI (600).

In some variations, a face distance display region (712) may be configured to guide the patient to position their face within a predetermined distance of the optical sensor. For example, a predetermined portion (e.g., between about 30% and 60%) of an image can include the face. For example, the face distance display region (712) may output a scale of distances relative to the optical sensor (e.g., too far, far, optimum, close, too close) in real-time. Additionally or alternatively, a face distance and/or a predicted physiological parameter may be communicated using one or more visual, audio, and haptic methods in a similar manner as described with respect to GUI (600). In some variations, face distance measurements outside the predetermined range may include noise or not contain sufficient information so as to reduce the accuracy of a physiological parameter prediction. In some variations, a physiological parameter prediction may be performed only when the measured face distance is within a predetermined range. As described in more detail herein, the methods described herein may be configured to differentiate between a face (713) of the patient and background (711).

Figure 8:
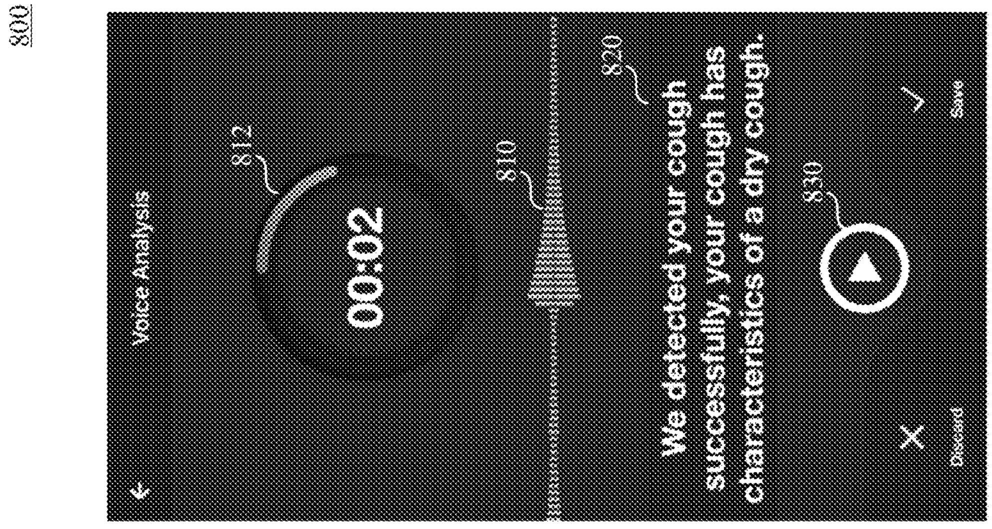
FIG. 8 is an illustrative variation of a graphical user interface relating to patient monitoring of a cough.

FIG. 8 depicts a graphical user interface (800) relating to patient monitoring of a cough. In some variations, audio output of the patient may be measured using an audio sensor such as a microphone of a computing device (e.g., smartphone, webcam, laptop). In some variations, the GUI (800)

may comprise an audio display region (810) configured to output a representation of the audio signal (e.g., waveform) recorded by the audio sensor in real-time. In some variations, a timer display region (812) may be configured to output one or more of an elapsed time of the recording and an estimate of the time remaining for cough parameter prediction. In some variations, the GUI (800) may comprise one or more cough parameter predictions (820). In some variations, the cough parameter may comprise one or more of a cough, a non-cough, a dry cough, and a wet cough. The physiological parameter predictions may be output in the GUI (800) using one or more alphanumeric characters, symbols, colors, image, and graphics in a similar manner as described with respect to GUIs (600, 700). For example, a cough prediction (820) may be output in one or more sentences. In some variations, the audio signal may be output (e.g., replayed) using a play icon (830).

Figure 9:
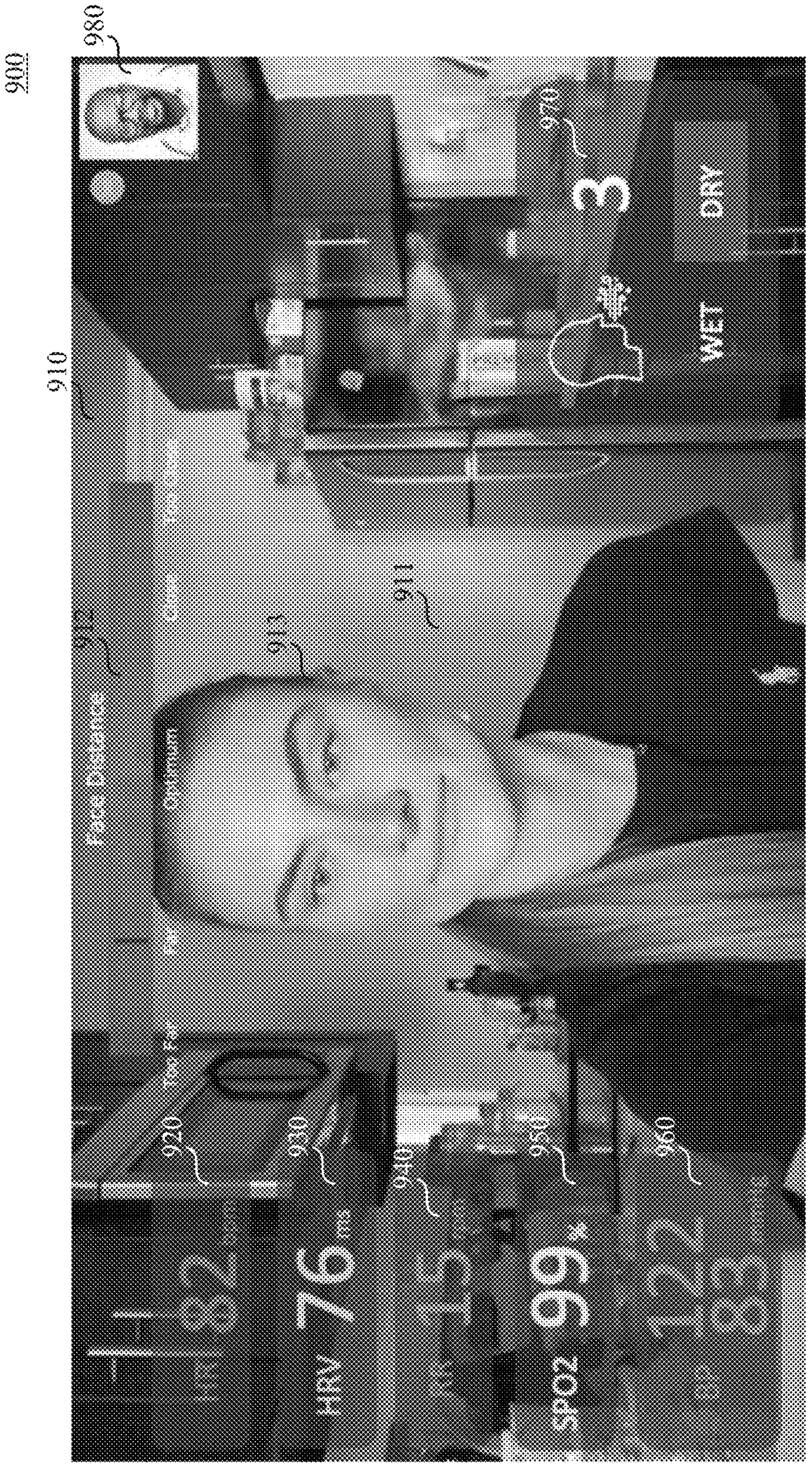
FIG. 9 is yet another illustrative variation of a graphical user interface relating to patient monitoring during a video conference.

FIG. 9 depicts a graphical user interface (900) relating to patient monitoring on a video conference. In some variations, the patient may be instructed to position their face within range of an optical sensor such as a web cam, smartphone camera, and the like. In some variations, the GUI (900) may comprise an optical sensor display region (910) configured to output the image signal (e.g., video) recorded by the optical sensor in real-time. In some variations, the GUI (900) may comprise one or more physiological parameter predictions (920, 930, 940, 950, 960, 970). For example, the predictions may be overlaid above the optical sensor display region (910). As shown in FIG. 9, the GUI (900) may comprise a heart rate display region (920), a heart rate variability display region (930), a respiratory rate display region (940), an oxygen saturation display region (950), a blood pressure display region (960), and a cough display region (970). In some variations, the physiological parameter predictions may be output in the GUI (900) using one or more alphanumeric characters, symbols, colors, image, and graphics in a similar manner as described with respect to GUIs (600, 700, 800).

In some variations, a face distance display region (912) may be configured to guide the patient to position their face within a predetermined range of the optical sensor. For example, the face distance display region (912) may output a scale of face distances relative to the optical sensor (e.g., too far, far, optimum, close, too close) in real-time. Additionally or alternatively, a face distance and/or a predicted physiological parameter may be communicated using one or more visual, audio, and haptic methods in a similar manner as described with respect to GUIs (600, 700, 800). In some variations, a physiological parameter prediction may be performed only when the measured face distance is within a predetermined range. As described in more detail herein, the methods described herein may be configured to differentiate between a face (913) of the patient and a background (911). In some variations, a web conference application such as a web browser may perform a majority (e.g., about 80%) of the computational load locally. Additionally or alternatively, one or more portions of processing and/or prediction may be encrypted and transmitted for remote processing and/or prediction.

Optionally, a trend of one or more of the physiological parameters may be generated based on a set of physiological parameters predicted over time (150). For example, a plot of a patient's blood pressure over time may be generated and output on a display. This may enable a patient's health status to be monitored and analyzed over time for one or more of diagnosis and treatment. In some variations, the predicted physiological parameter data may be merged with other data sets (e.g., nutrition, drug, activity, etc.). Trend analysis of one or more data sets may provide holistic insight for one or more of a patient, health care professional, family, support group of the patient's health over time. For example, a thirty second selfie video of the face may be used to assess a change in a patient's real-time health status or if there is an increased risk for an adverse event that may be notified to the patient's health care professional. In some variations, a GUI may be configured to output one or more of a real-time physiological parameter prediction, historical physiological parameter prediction, and physiological parameter trends (e.g., lower blood pressure).

In some cases, the patient's predicted data and trends may be used by one or more of the patient and health care professional to take action to improve health outcomes. The results of the analysis may be used to generate one or more prompts to output to the patient and/or health care professional. For example, data analysis showing that a patient is exhibiting a potentially dangerous trend may be the basis to output a GUI notification advising them to schedule an appointment with a health care professional, change diet habits, and/or add an activity notification through their computing device to encourage more physical activity. Additionally or alternatively (e.g., concurrently), a GUI notification may be output to the patient's health care professional, family members, and/or other support group notifying them of the patient's condition and optionally suggesting appropriate intervention steps. As another example, data analysis showing that a patient is on a positive trend may be used to generate a prompt providing positive reinforcement to the patient.

A. Finger Image Signal

Figure 2:
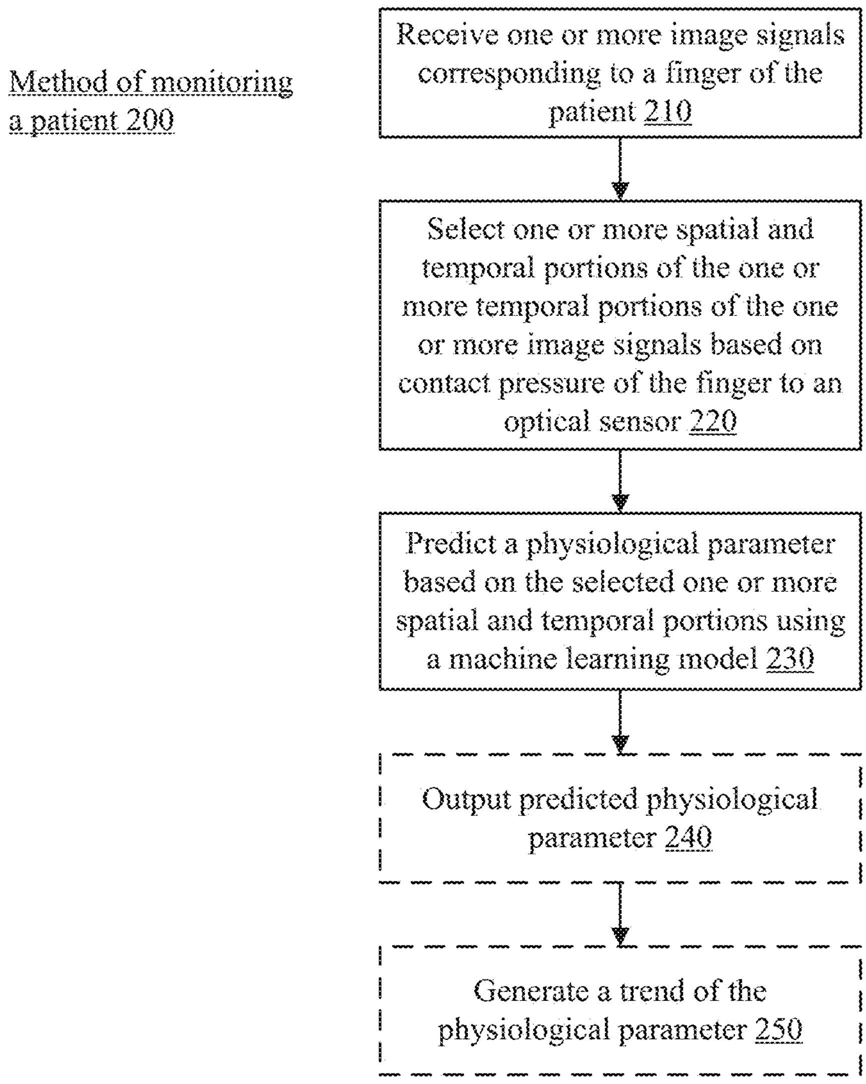
FIG. 2 is a flowchart of an illustrative variation of a method of monitoring a physiological parameter of a patient using a finger.

FIG. 2 is a flowchart depicting an illustrative variation of a method of monitoring a physiological parameter using a finger of a patient (200). When an image signal corresponds to a finger of the patient (e.g., pressed against an optical sensor), the methods of monitoring a physiological parameter may generally comprise receiving one or more image signals corresponding to a finger of the patient (210). In some variations, one or more spatial and temporal portions of one or more of the image signals may be selected based on a contact pressure of the finger to an optical sensor (220). For example, image signals having a contact pressure outside a predetermined pressure range may be discarded. Additionally or alternatively, one or more of the image signals may be processed based on a shutter speed and signal gain of an optical sensor associated with one or more of the signals as described herein.

In some variations, one or more physiological parameters may be predicted based on the selected one or more spatial and temporal portions using a machine learning model (230). The machine learning model of method (200) may comprise any of the second machine learning models described herein. Optionally, the predicted physiological parameter may be output (240) in a similar manner as described with respect to FIGS. 1 and 6-9. Optionally, a trend of one or more of the physiological parameters may be generated based on a set of physiological parameters predicted over time (250) as described herein.

i. Heart Rate Variability

In some variations, the physiological parameter may comprise heart rate variability (HRV). Generally, heart rate variability corresponds to the variation in a time interval between consecutive heartbeats as measured in milliseconds. An accuracy of a heart rate variability prediction may depend on the correct prediction of a set of peak locations of a set of cardiac cycles. In some variations, the heart rate variability may comprise one or more of a standard deviation of NN intervals (SDNN), a mean of the NN (e.g., peak-to-peak distance) intervals, and a root mean square of successive differences between normal heartbeats (RMSSD).

Figure 14B:
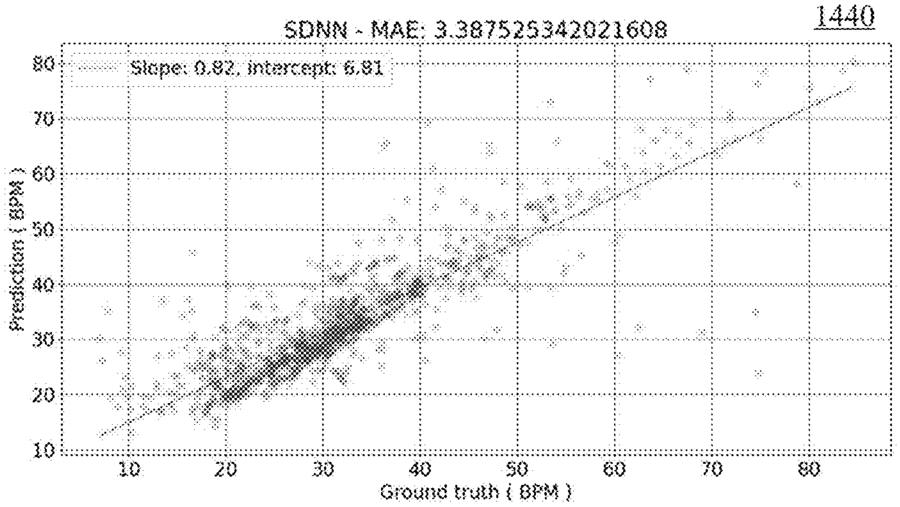
FIG. 14B are plots of an illustrative variation of heart rate variability prediction errors.
Figure 14B:
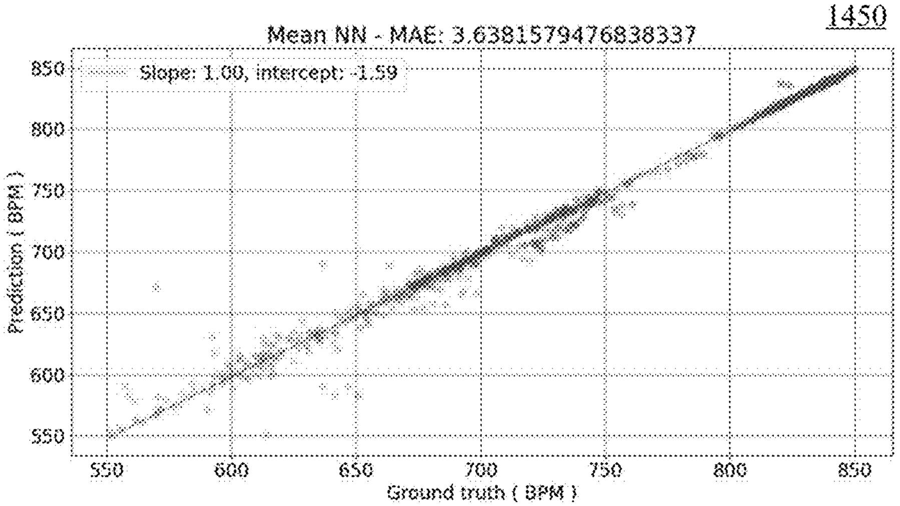
Figure 14B:
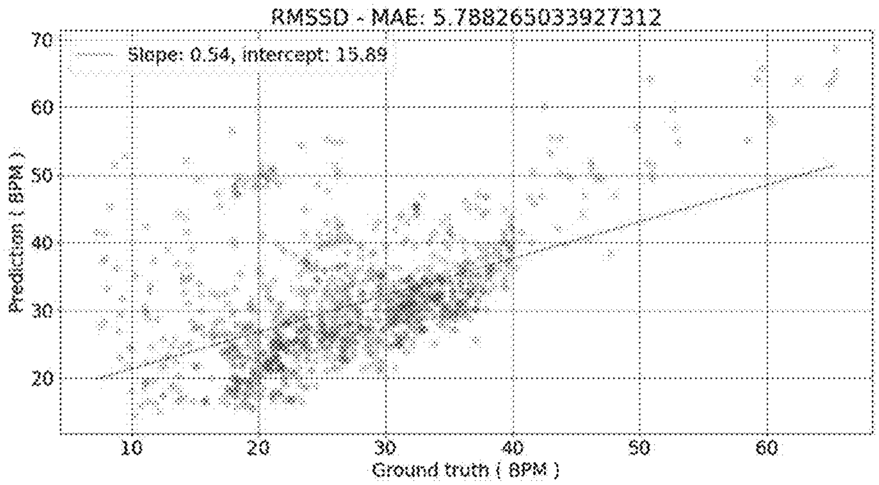

In some variations, predicting the physiological parameter may comprise extracting a set of color channels (e.g., red, green, blue) from the processed one or more image signals and identifying a set of peak locations. For example, each color channel may be weighted by the variance of a predetermined number of frames (e.g., about the last 100 frames). In some variations, a set of peak locations may be identified by calculating a first derivative of one or more of the image signals. In some variations, one or more of the image signals may be quadratically upsampled around the peaks identified from the calculated first derivative to compensate for a lower sampling rate of the image signals. Noisy peaks having an amplitude lower than a predetermined percentage of the median amplitude of the peaks may be discarded. Diastolic and other noisy peaks where consecutive peaks having a distance of less than about 500 milliseconds may be discarded. The remaining peak locations may be used to predict heart rate variability based on peak-to-peak distances. FIG. 14B are plots of heart rate variability prediction errors for SDNN (1440), mean of the NN (1450), and RMSSD (1460).

B. Face Image Signal

Figure 3:
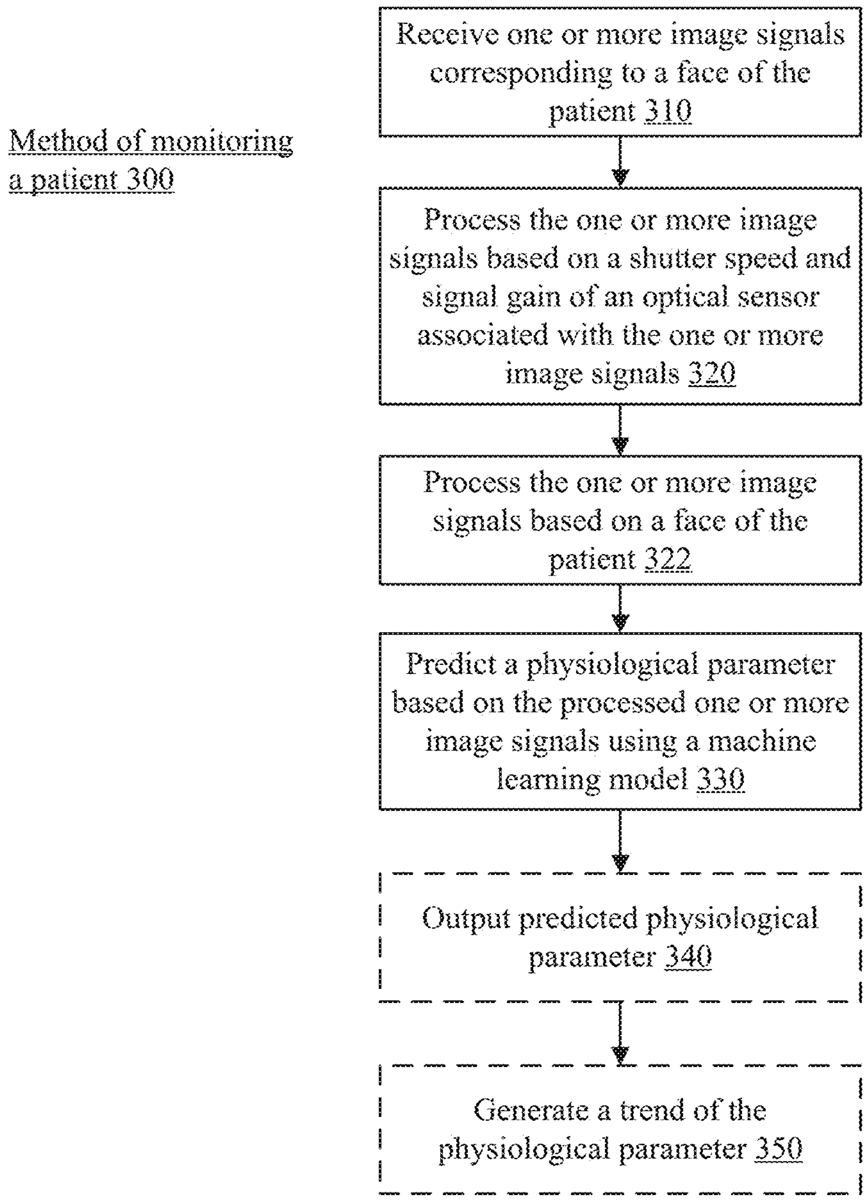
FIG. 3 is a flowchart of an illustrative variation of a method of monitoring a physiological parameter of a patient using a face.

FIG. 3 is a flowchart depicting an illustrative variation of a method of monitoring a physiological parameter using a face of a patient (300). When an image signal corresponds to a face of the patient, the methods of monitoring a physiological parameter may generally comprise receiving one or more image signals corresponding to a face of the patient (310). In some variations, one or more of the image signals may be processed based on a shutter speed and signal gain of an optical sensor associated with one or more of the signals (320), as described herein.

Figure 15:
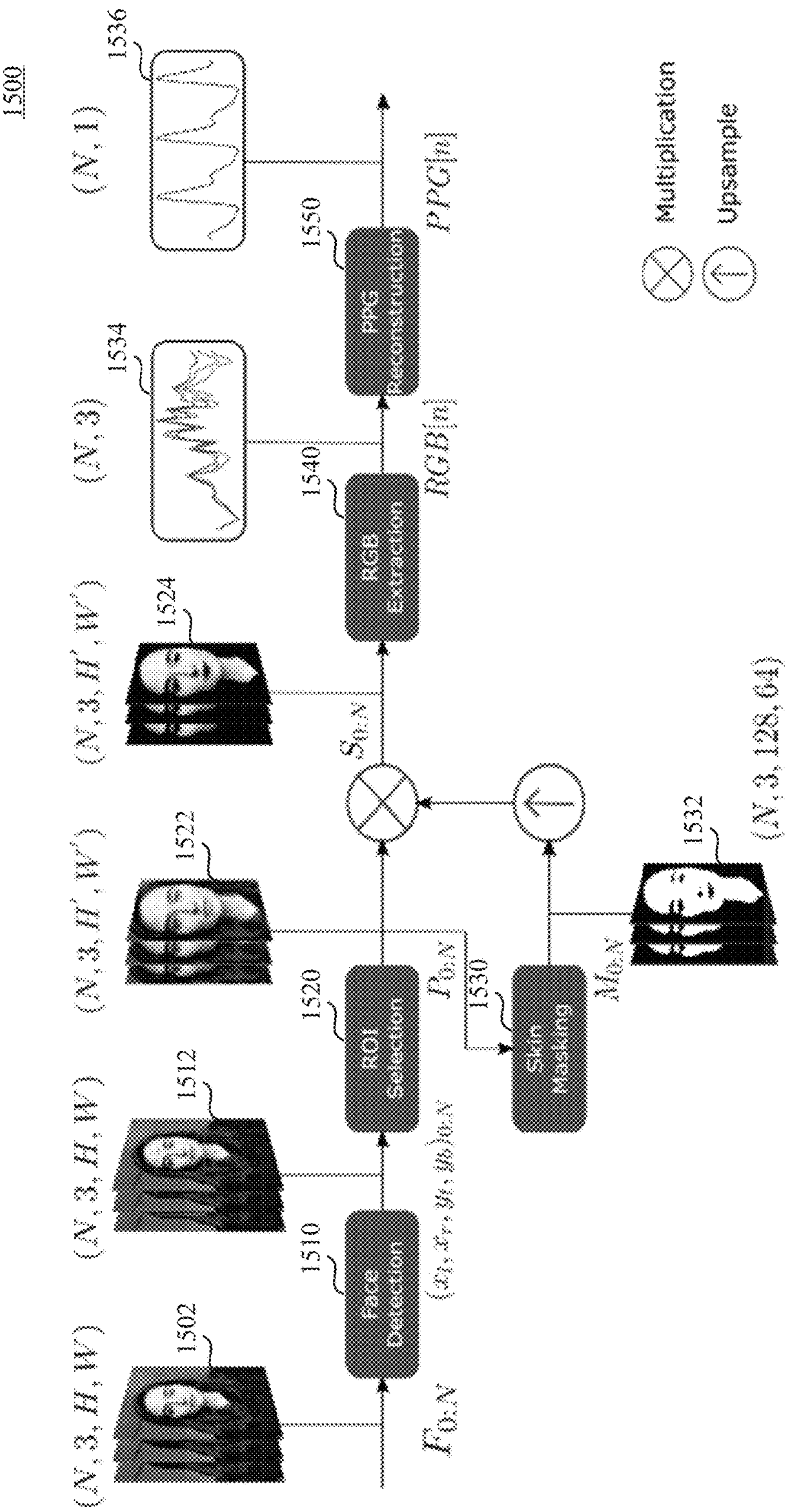
FIG. 15 is a block diagram of an illustrative variation of facial image processing.
Figure 17:
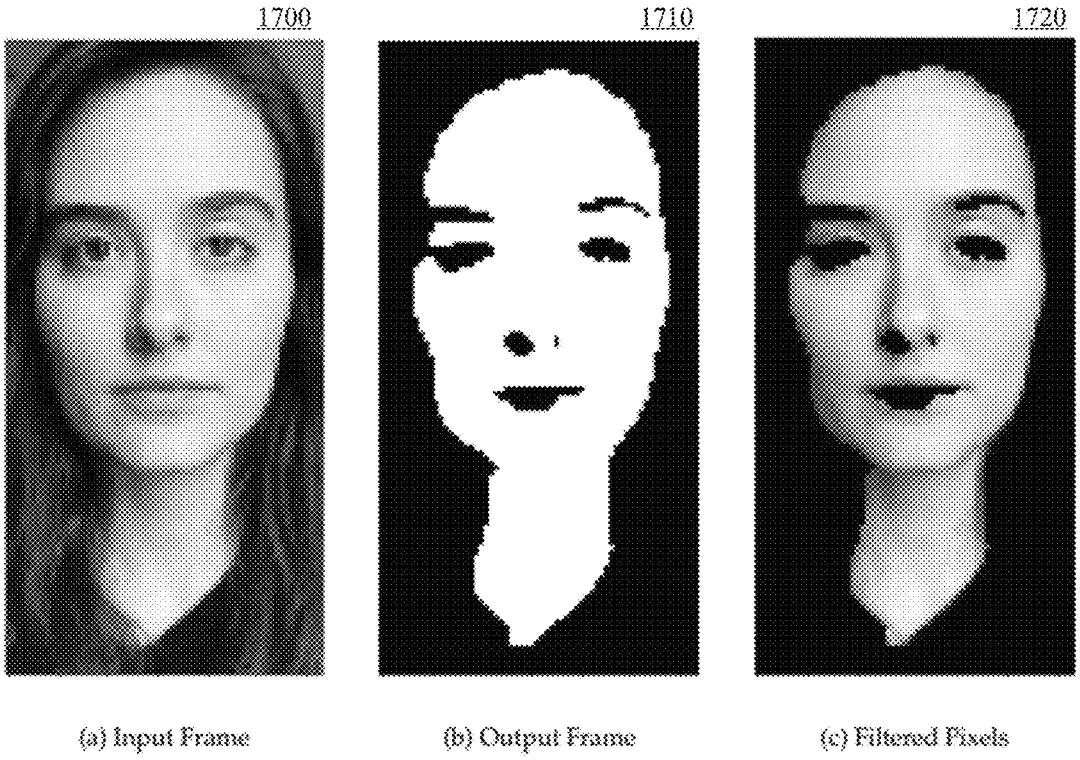
FIG. 17 is a set of images of an illustrative variation of a skin masking process.

In some variations, one or more of the image signals may be processed based on a face of the patient (322). For example, a face of the patient may be extracted from the image signal and used to generate a PPG signal for physiological parameter prediction. FIG. 15 is a block diagram of facial image processing (1500) of received image signals (1502) (e.g., video frames F). Input frame (1700) of FIG. 17 is an example of a received image signal. In some variations, a face of the received image signals (1502) may be detected (e.g., selected, identified) using a face detection module at step 1510 (e.g., for each frame of video). For example, the face output (1512) may include bounding box coordinates ($x_l$, $x_r$, $y_t$, $y_b$).

The face output (1512) of the face detection step 1512 may be input for a region of interest (ROI) selection module at step 1520. In some variations, a neck of the patient may be detected based on the detected face at step 1520. A face and neck output (1522) of the ROI selection step 1520 may include the selected face and neck of the patient. That is, the selected skin pixels of the image signal may include both the face and the neck of the patient selected from the image signals F. In some variations, the face and neck output (1522) may include a set of padded bounding boxes P.

Figure 16A:
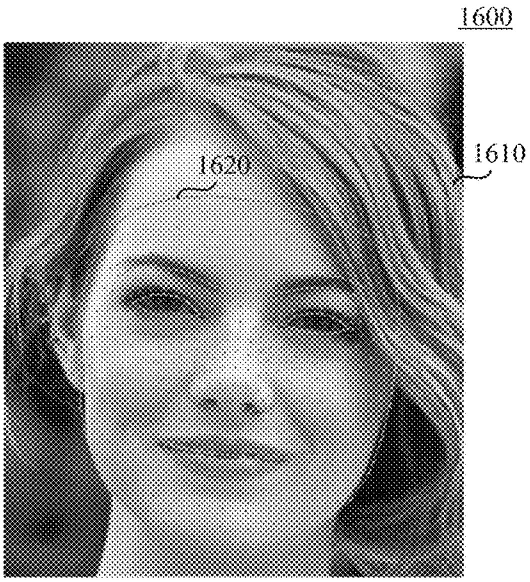
FIG. 16A is an image of an illustrative variation of facial image detection.
Figure 16B:
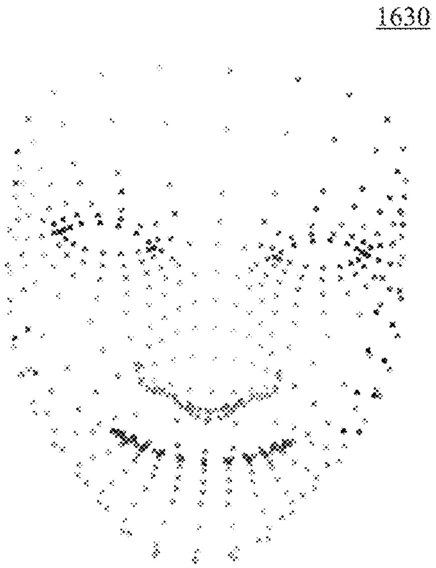
FIG. 16B is an image of an illustrative variation of a face mesh.

Additionally or alternatively, a face of the patient may be processed (e.g., detected) by generating a face mesh. FIG. 16A is an image (1600) of facial image detection including a face mesh (1620) corresponding to a face of a patient (1610). FIG. 16B is another image of a face mesh (1630) corresponding to face mesh (1620) of the image (1600).

In some variations, the detected face and neck may be subsequently processed together in steps 1530-1550. In some variations, the face and neck output (1522) may be input to a skin masking module at step 1530 to generate a skin mask output (1532, M, 1710).

In some variations, the skin masking module may comprise a machine learning model (e.g., U-Net model) configured to predict whether each pixel from the face and neck output (1522) corresponds to skin (as opposed to other features such as hair, eyes, glasses, etc.). The output of the machine learning model may comprise a probability map of skin predictions. A predetermined threshold compared to the probability map may be used to generate a skin mask output (1710). For example, output frame (1710) of FIG. 17 is an output frame of the skin masking step 1530 including a face and neck. The face and neck output (1522) may be processed with the skin mask output (1532) to generate a filtered output (1524, S). For example, the skin mask and padded frames may be combined to filter skin-only images S (e.g., to remove non-skin pixels). As shown in FIG. 17, filtered pixels (1720) show skin pixels of just the face and neck, with all other pixels (e.g., background, eyes, hair, clothes, etc.) removed.

In some variations, an RGB extraction module at step 1540 extracts a mean RGB signal (1534) from the input filtered output (1524). In this manner, a patient's image data is anonymized (e.g., identifiable features are removed) to enhance privacy and reduce computational load. In some variations, the RGB extraction step 1540 may comprise applying a z-normalization separately to a plurality of sliding windows of the mean RGB signal. In some variations, z-normalization comprises per temporal point normalization with respect to a local neighborhood.

Figure 21:
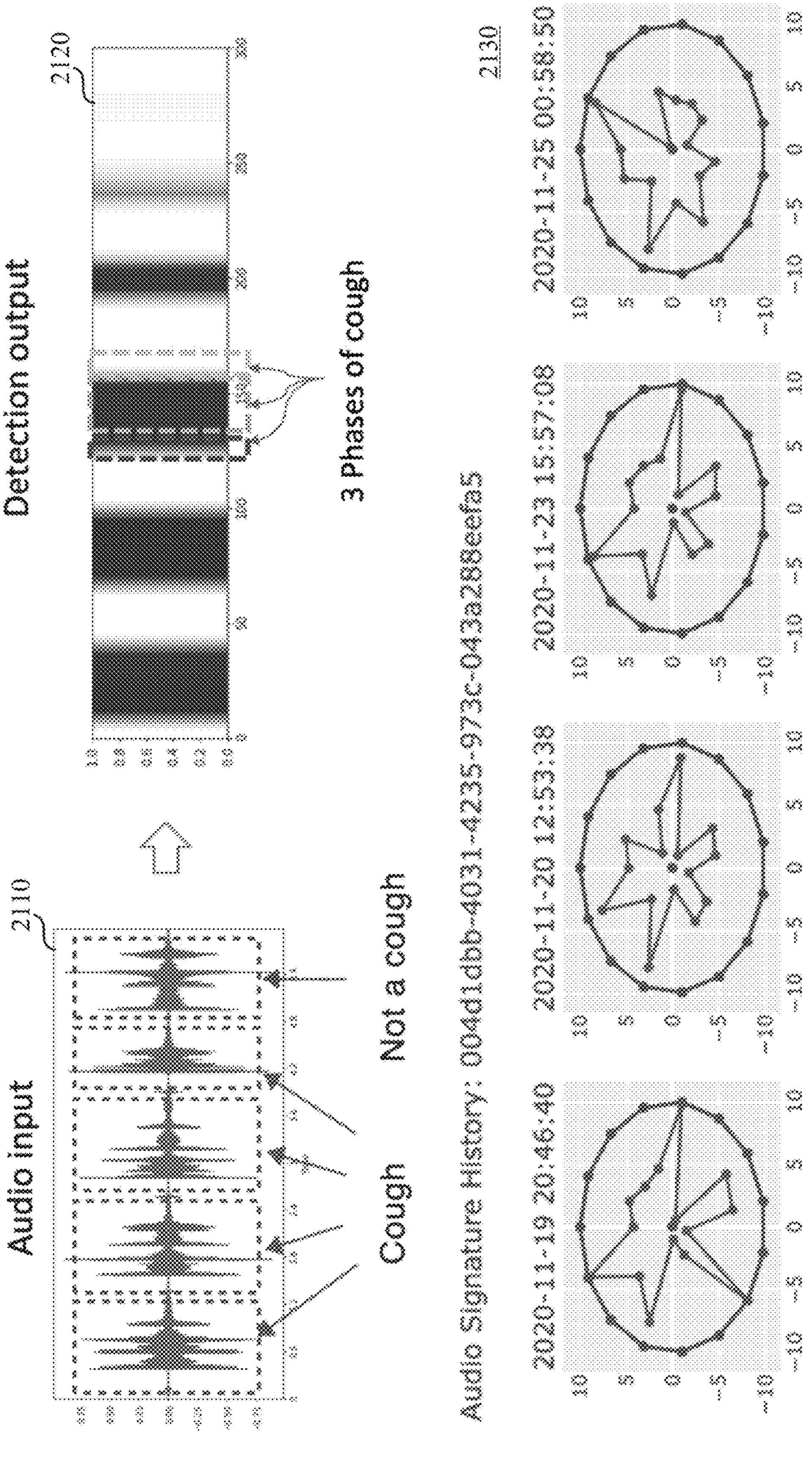
FIG. 21 are plots of an illustrative variation of voice processing.

In some variations, the PPG reconstruction module at step 1550 includes inputting the mean RGB signal (1534) to a first machine learning model to generate a PPG signal (1536). For example, the first machine learning model may comprise an autoencoder (2100) as shown in FIG. 21 where a mean RGB signal corresponding to a face of the patient is input and a PPG signal is output. The autoencoder may have residual connections and have similar architecture to BuriGNet. A performance comparison of the autoencoder (AE) model against a set of other RGB to PPG models (e.g., CHROM, POS, VQVAE) is shown in the table (2150) of FIG. 21. In some variations, the first machine learning model may comprise a vector quantized autoencoder.

In some variations, an RGB timeseries signal may be processed by a first machine learning model to output a PPG signal. For example, the face mesh (1630) of FIG. 16B may be used to generate an RGB timeseries signal for each pixel of the face mesh (1630). In some variations, the RGB timeseries signal may be input to one or more of a graph convolutional network and graph attention network to generate a PPG signal.

In some variations, the first machine learning model of step 1550 may comprise a WaveResNet model. For example, the first machine learning model may comprise a chain of convolutions of increasing dilations with depth forming a basis for a building block. The dilations may be reset at the beginning of each block where the blocks are connected with residual connections (e.g., in a manner similar to ResNet). The WaveResNet model may not change input size while processing and may be used for signal transformation (e.g., mean RGB signal to PPG signal).

In some variations, the first machine learning model of step 1550 used to generate a PPG signal may be trained using a FFT-loss function to compensate for shifting due to synchronization methods used for data recording. For example, a phase variable (Δt) may be introduced in model training to represent an amount of shift between a ground truth signal and an input signal. The shift property may be expressed as:

$$FFT[x(t)] = X(f)$$

$$FFT[x(t+\Delta t)] = \exp(i2\pi f\Delta t)X(f)$$

The original signal may be rewritten as the FFT loss function x(t+Δt):

$$\begin{aligned} x(t+\Delta t) &= IFFT[\exp(i2\pi f\Delta t)FFT[x(t)]] \\ &= IFFT[\cos(2\pi f\Delta t)FFT[x(t)] + i\sin(2\pi f\Delta t)FFT[x(t)]] \end{aligned}$$

In some variations, the loss function may be used with other losses such as MAE, MSE, Pearson loss, and the like.

In some variations, the first machine learning model of step 1550 may comprise one or more of self-supervised learning and semi-supervised learning. Self-supervised learning may comprise labeling a set of face image signals to create a network that can learn from an unlabeled set of face image signals. Semi-supervised learning may comprise sampling two consecutive and partially overlapping windows of mean RGB signals. The model generates a PPG signal and a distance (e.g., L1 distance, Pearson loss, MSE, etc.) between overlapping parts may be minimized with a gradient based approach. For a predetermined number of batches (e.g., 10 batches), one batch of labeled data may be processed accordingly. For the labeled data, there is an additional loss of distance between the ground truth signal and predicted PPG signal. In this manner, the network may learn from unlabeled image signals while labeled image signals direct the learning process towards a more accurate function. Furthermore, semi-supervised learning may naturally lead the model to generate temporally consistent predictions due to the overlapping windows.

Albedo Image Processing

In some variations, image illumination may affect an accuracy of a predicted PPG signal. The reflection of light may generally be categorized into specular reflection and diffuse reflection. Specular reflection corresponds to light reflected from a smooth surface at a predetermined angle while diffuse reflections is produced by rough surface that tend to reflect light in all directions. PPG information may be encoded within a diffuse portion of the reflected light in an image signal and the specular portion of the reflected light may be considered noise. In some variations, facial image processing may comprise decomposing an image comprising a face based on shape, reflectance, and illumination. For example, an input image (1900) may be decomposed into a normal image (1910), albedo image (1920), a shading image (1930), and a vector specifying the extracted lighting. A masked albedo image may be generated based on the albedo image and a skin mask and used to generate a PPG signal as described herein.

Figure 18:
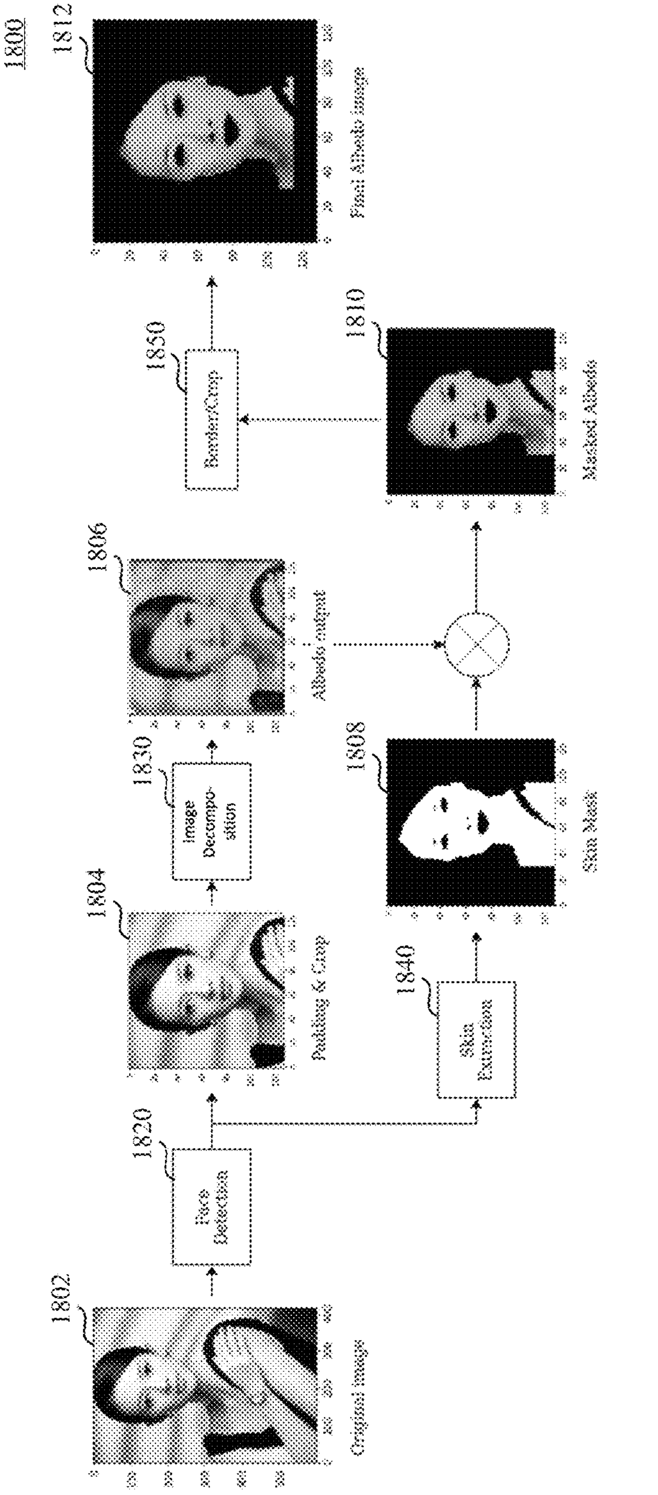
FIG. 18 is a block diagram of an illustrative variation of albedo image processing.
Figure 19:
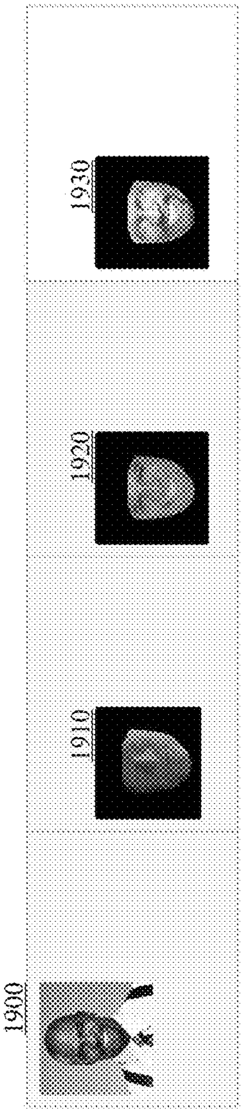
FIG. 19 is a set of images of an illustrative variation of albedo image processing.
Figure 20:
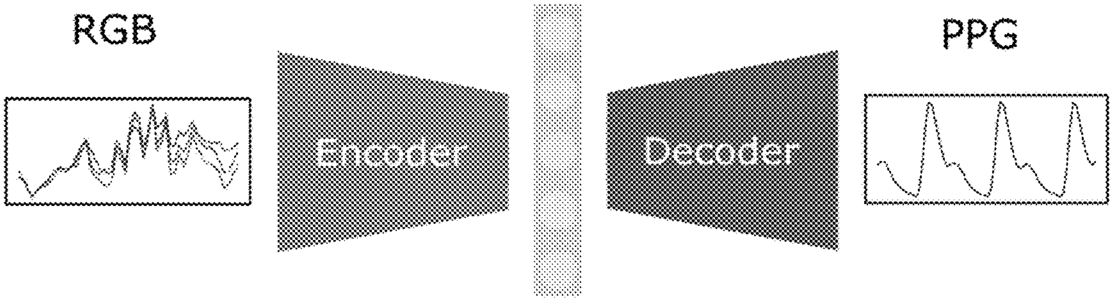
FIG. 20 is a block diagram of an illustrative variation of PPG signal generation from mean RGB signals.

FIG. 18 is a block diagram of albedo-based facial image processing (1800) of received image signals (1802). In some variations, a face of the received image signals (1802) may be detected (e.g., selected, identified) using a face detection module at step 1820 (e.g., for each frame of a video). For example, the face output (1804) may be padded and cropped. In some variations, a neck of the patient may be detected based on the detected face at step 1820 such that the face output (1804) also includes the neck of the patient.

The face output (1804) of the face detection step 1820 may be input for an image decomposition module at step 1830. For example, the face output (1804) may be decomposed into one or more of a normal image, albedo image (1806), a shading image, and a vector specifying the extracted lighting. In some variations, the albedo image may include diffuse reflection and may be substantially absent specular reflection.

In some variations, the face (and neck) output (1804) may be input to a skin extraction (e.g., masking) module at step 1840 to generate a skin mask output (1808). In some variations, the skin masking module may comprise a machine learning model as described herein. The skin mask output (1808) may comprise a face and neck. The albedo output (1806) may be processed (e.g., multiplied) with the skin mask output (1808) to generate a filtered output (1810) (e.g., masked albedo image). For example, the skin mask and albedo image may be combined to remove non-skin pixels. Optionally, the filtered output (1810) may be input to a border/crop module at step 1850 to generate a filtered output (1812) (e.g., final albedo image). The filtered output (1810, 1812) may be processed by an RGB extraction module and/or PPG reconstruction module as described with respect to FIG. 15 to generate a PPG signal.

Turning back to FIG. 3, one or more physiological parameters may be predicted based on the processed one or more image signals using a machine learning model (330). The machine learning model of method (300) may comprise any of the machine learning models described herein. In some variations, the first machine learning model training set is trained with a self-supervised learning mean RGB training set comprising artificial noise comprising one or more of Gaussian noise, Gaussian blur, cropping, and cutout. Optionally, the predicted physiological parameter may be output (340) in a similar manner as described with respect to FIGS. 1 and 6-9. Optionally, a trend of one or more of the physiological parameters may be generated based on a set of physiological parameters predicted over time (350) as described herein.

C. Hybrid Image Signal

Figure 4:
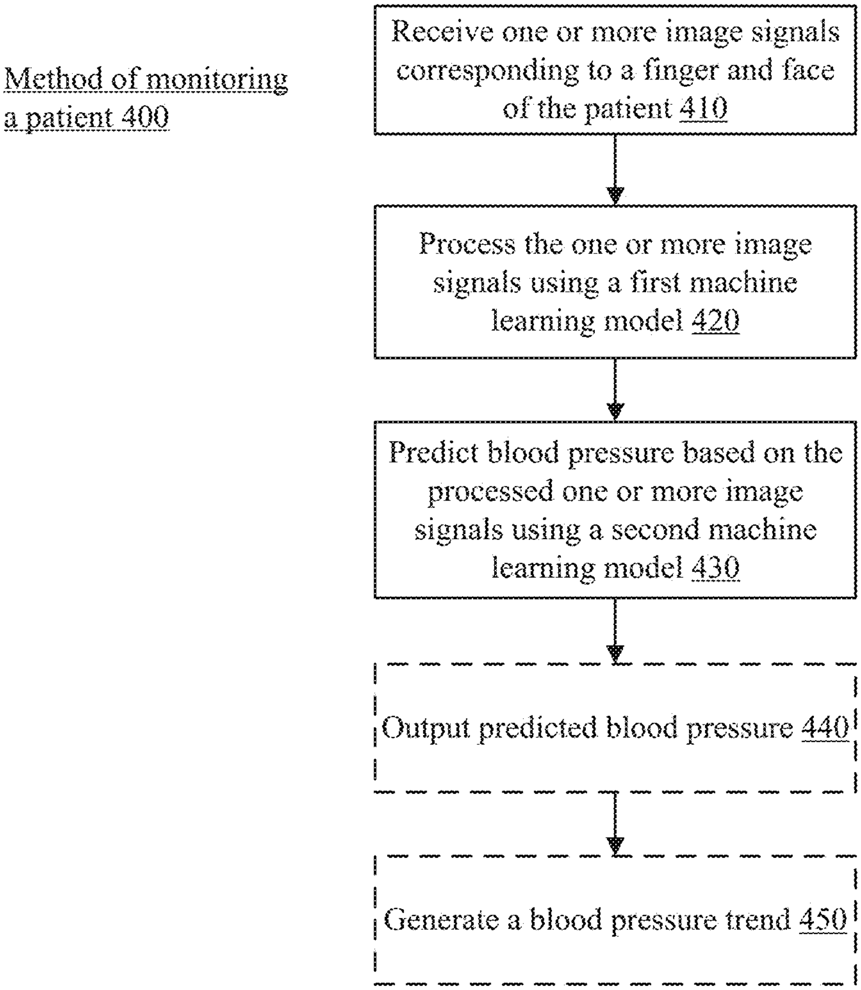
FIG. 4 is a flowchart of an illustrative variation of a method of monitoring blood pressure of a patient using a finger and face.

FIG. 4 is a flowchart depicting an illustrative variation of a method of monitoring a physiological parameter (e.g., blood pressure) using a finger and a face of a patient (400). The accuracy of the predicted physiological parameters may be increased by analyzing the combination of the finger image signal and face image signal. When the image signals correspond to a finger and a face of the patient, the methods of monitoring a physiological parameter may generally comprise receiving one or more image signals corresponding to the finger and face of the patient (410). In some variations, a finger image signal may be generated using a rear-facing camera of a smartphone and a face image signal may be generated using a front-facing camera (e.g., selfie-camera) of a smartphone for a predetermined amount of time (e.g., at least about 12 seconds).

In some variations, one or more of the image signals may be processed using a first machine learning model (420). The first machine learning model of method (400) may comprise any of the first machine learning models described herein.

In some variations, blood pressure may be predicted based on the processed one or more image signals using a second machine learning model (430). The second machine learning model of method (400) may comprise any of the second machine learning models described herein. For example, a predicted blood pressure may be based on a combination of a plurality of predicted blood pressure prediction methods as described herein including both fingertip and face image signals. In some variations, blood pressure may be predicted based on a pulse transit time (PTT) calculated between two predicted PPG signals via triangulation and phase estimation.

Some optical sensors, such as smartphone cameras, use a rolling shutter method of capturing images where a frame of video is captured by scanning a scene rapidly (e.g., scanning from top to bottom sequentially) and not in a single point in time. For example, an upper portion (e.g., forehead) of an image may comprise pixels taken before a lower portion (e.g., chin) of the image. However, a cardiac beat traveling from the heart to the head appears first in a lower portion of a face image before the upper portion of the image. In some variations, a face image may be divided into n rows where a mean RGB signal and PPG signal are generated for each row. A PTT may be calculated between adjacent rows to create a set of blood pressure estimates. In some variations, a PPG signal may be generated for each of a forehead portion and chin portion of the image for two consecutive frames of an image signal.

In some variations, a set of blood pressure predictions may be merged into a single blood pressure prediction using one or more machine learning-based methods, sensor fusion techniques (e.g., Kalman filters), and belief theories (e.g., Dempster-Shafer theory).

Optionally, the predicted physiological parameter may be output (440) in a similar manner as described with respect to FIGS. 1 and 6-9. Optionally, a trend of one or more of the physiological parameters may be generated based on a set of physiological parameters predicted over time (450) as described herein.

D. Audio Signal

Figure 5:
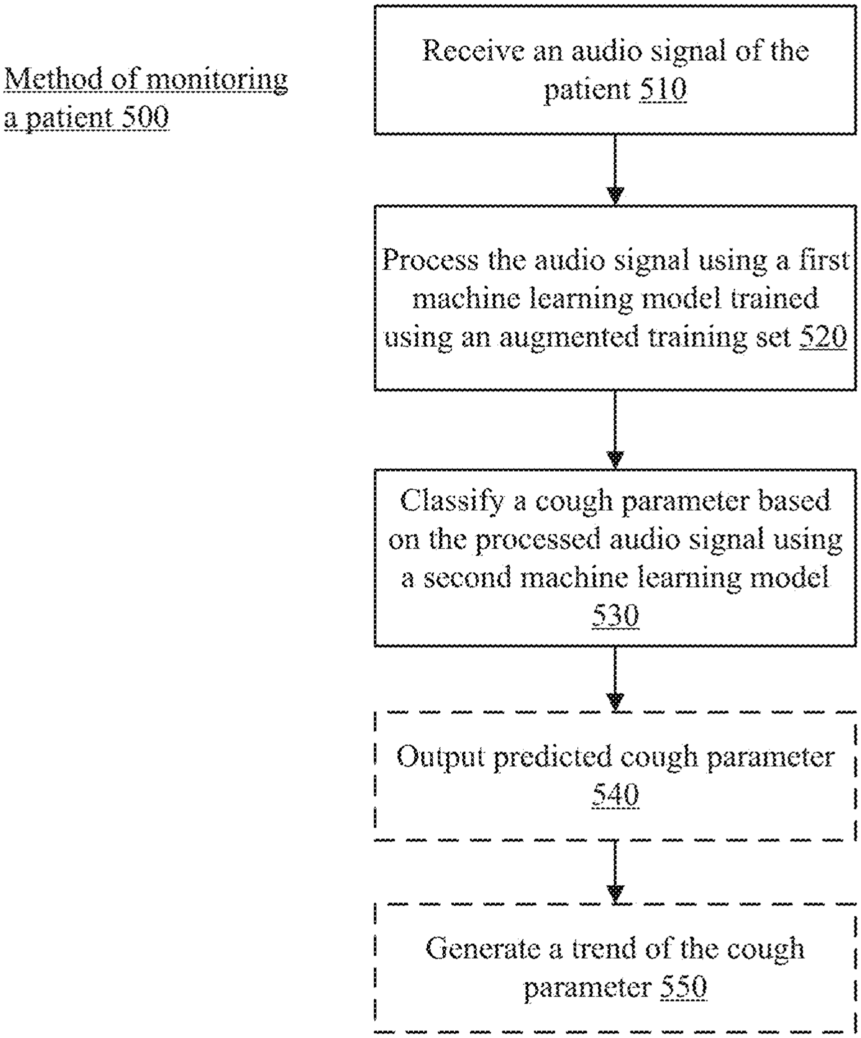
FIG. 5 is a flowchart of an illustrative variation of a method of monitoring a cough of a patient.

In some variations, the physiological parameter to be predicted may be one or more of cough parameters based on an audio signal of a patient. For example, one or more cough parameters such as a number and a type of cough (e.g., wet, dry, no cough) may be estimated based on a voice profile of the patient. FIG. 5 is a flowchart depicting an illustrative variation of a method of monitoring a voice of a patient (500). In the variation depicted in FIG. 5, the method may comprise receiving an audio signal of the patient (510). In some variations, the audio signal may be generated by an audio sensor (e.g., microphone). For example, a microphone of a smartphone may record an audio signal corresponding to audio output of the patient (including silence). In some variations, an audio signal may have a length of between about 300 milliseconds and about 10 seconds.

The audio signal may be processed using a first machine learning model using an augmented training set (520). The first machine learning model of method (500) may comprise any of the first machine learning models described herein. For example, the first machine learning model may comprise one or more of a residual neural network (ResNet), a convolutional neural network, a hybrid binary and multiclass classification model, and combinations thereof. In some variations, the first machine learning model comprises supervised learning.

In some variations, a ResNet model may comprise a ResNet50, variational ResNet50, and ResNet18 (e.g., distillation learning with ResNet50). For example, the ResNet50 model may comprise convolutional layers, fully connected sequential layers (e.g., linear layer with ReLu, dropout, linear layer), a cross entropy loss function weighted based on the number of patient audio samples (e.g., weighted inversely proportional to number of patient audio samples), and a parameter optimizer (e.g., Adam). In some variations, a variational multiclass ResNet50 model may comprise a variational layer at the end of the model. In some variations, a ResNet18 model may comprise convolutional layers and fully connected sequential layers (e.g., linear layer with ReLu, dropout, linear layer). Distillation learning improved the learning capability of the ResNet18 model.

In some variations, a hybrid binary and multiclass classification model may comprise predetermined weighting. For example, cough detection may be weighted about 65% binary classification model and about 35% multiclass classification model, and wet/dry cough detection may be weighted about 85% binary classification model and about 15% multiclass classification model.

Figure 22A:
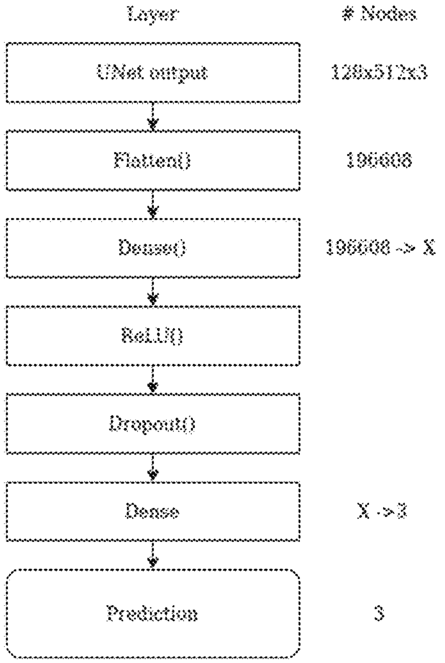
FIG. 22A is a block diagram of an illustrative variation of a U-Net model.

In some variations, the first machine learning model may comprise a U-Net model where the output is flattened and a dense layer with X nodes is added. For example, FIG. 22A is a block diagram of a U-Net model (2210) where three predictions are output.

Figure 22B:
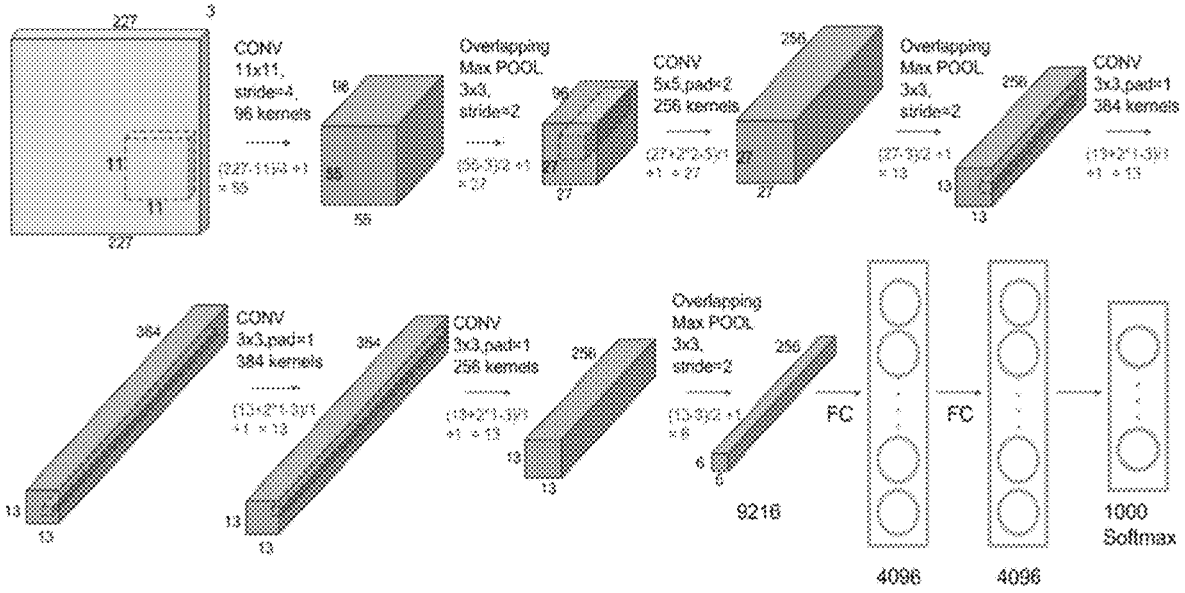
FIG. 22B is a block diagram of an illustrative variation of a AlexNet model.
Figure 22C:
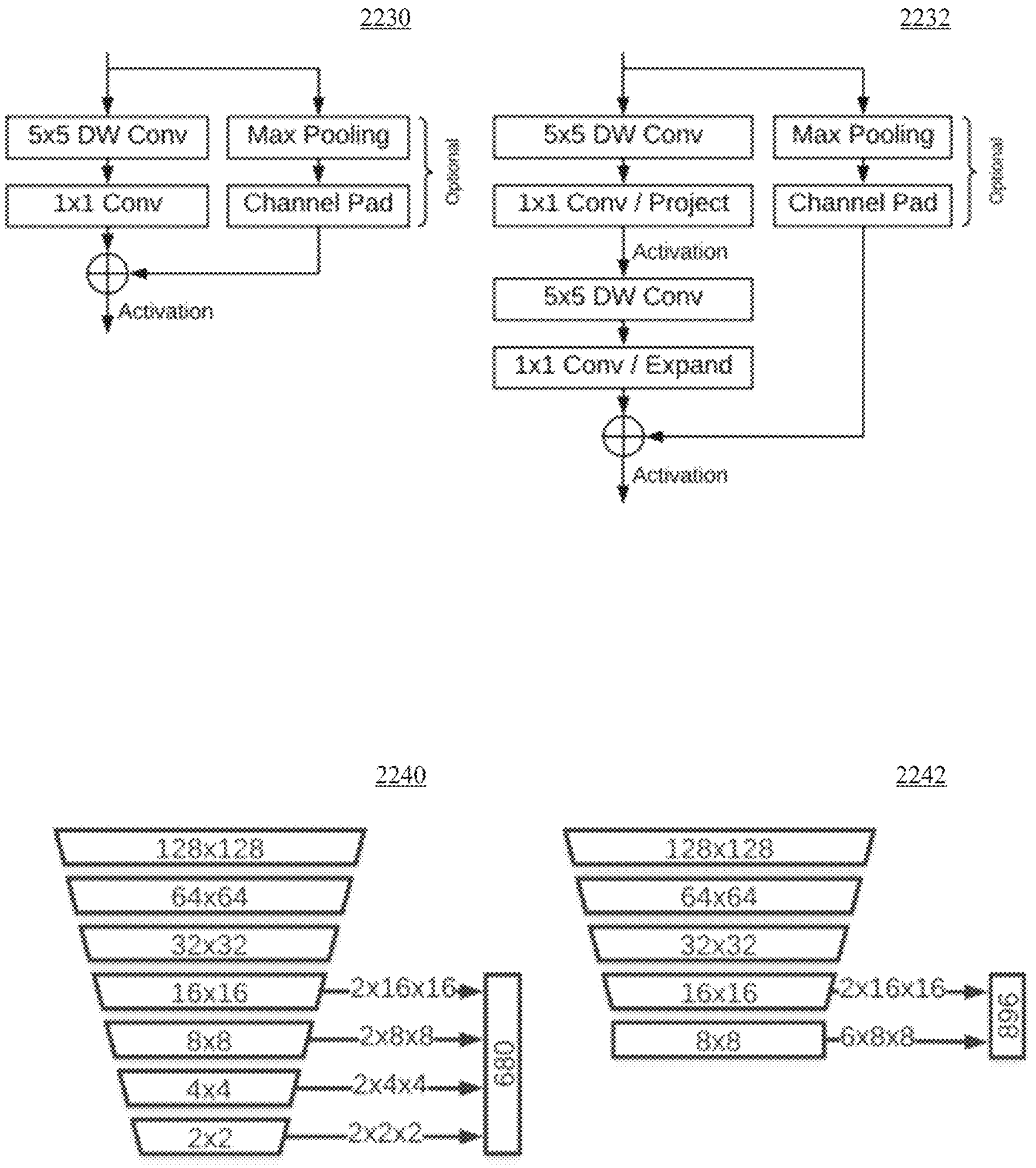
FIG. 22C is a block diagram of an illustrative variation of a BlazeFace model.

FIG. 22B is a block diagram of an AlexNet model (2220). FIG. 22C is a block diagram of an illustrative variation of a BlazeFace model including a BlazeBlock (2230) and double BlazeBlock (2232). The BlazeFace model may comprise a sequential fully connected layer to the end of the model including 2D adaptive average pooling and two linear layers. Anchor computations of an SSD model (2240) and BlazeFace model (2242) are shown for comparison.

In some variations, the augmented training set comprises artificial noise comprising one or more of Gaussian noise, white noise, frequency mask, time mask, pitch change, time shift, and time stretch. For example, white noise may include a randomly selected SNR value and randomly generated Gaussian noise with a mean of zero and standard deviation of one. A frequency mask or a time mask may be applied with a random max-width between about 5 and about 30 without using a mean and a probability of 50%. A pitch change of the audio signal may be changed randomly between about −5 and about 5. A time shift may divide the audio signal and concatenate the signal in reverse order. A time stretch may change a length of the audio signal uniformly at a predetermined percentage between 80% and 120%.

In some variations, processing the audio signal selects one or more portions of the audio signal. For example, silent portions or background noise (e.g., non-patient noise) may be removed from the audio signal.

In some variations, processing the one or more audio signals may comprise extracting a mel spectrogram from the audio signal. For example, one or more of a logarithm, first derivative, and a second derivative of the mel spectrogram may be calculated. FIG. 21 depicts are plots (2110, 2120) of voice processing and a patient audio signature history (2130).

A cough parameter may be classified based on the processed audio signal using a second machine learning model (530). In some variations, the cough parameter may comprise one or more of a cough, a non-cough, a dry cough, and a wet cough.

Optionally, the predicted cough parameter may be output (540) in a similar manner as described with respect to FIGS. 1 and 6-9. Optionally, a trend of one or more of cough parameters may be generated based on a set of cough parameters predicted over time (550) as described herein.

II. Devices

Overview

Also described here are systems that may include one or more of the components used to predict a physiological parameter. Generally, described herein is an artificial intelligence (AI) environment configured to process patient data and predict a set of vital signs. The AI environment may be accessible from a plurality of configurations such as a mobile platform (e.g., accessible through a mobile application executable on a mobile computing device such as a smartphone) as well as a web-based platform (e.g., accessible through a web browser on a laptop or desktop computing device). In these variations, a user may interact with the mobile and web-based platforms interchangeably. Furthermore, the AI environment may include a system of applications that allows services (e.g., web conference, web browser, telehealth) to integrate physiological parameter predictions in real-time for a set of users (e.g., patients, doctors).

Figure 23:
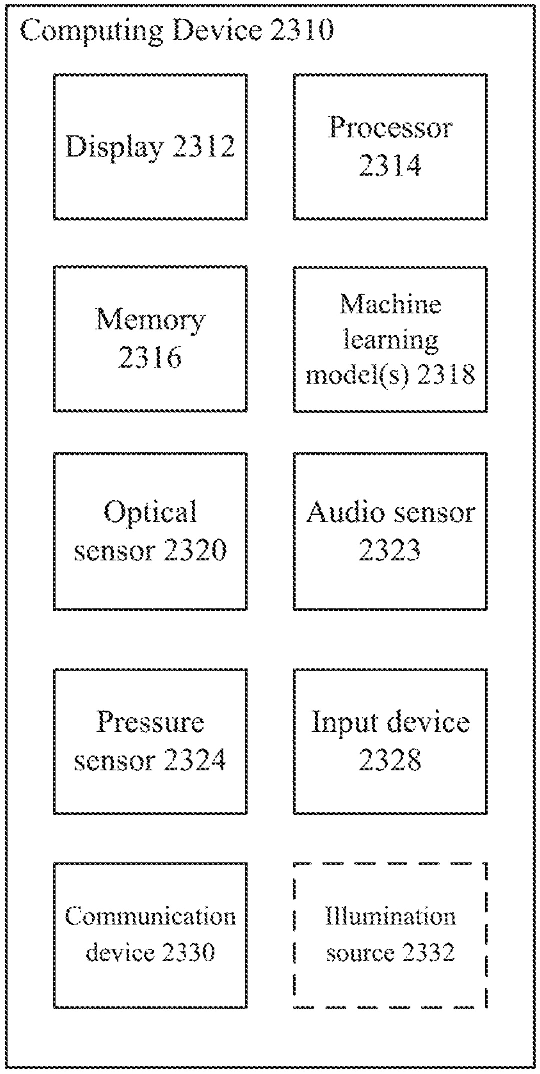
FIG. 23 is a block diagram of an illustrative variation of a computing device.

FIG. 23 is a block diagram of a computing device (2310) comprising the computing device (2310) may comprise one or more of a display (2312), processor (2314), memory (2316), machine learning model(s) (2318), optical sensor (2320), audio sensor (2322), pressure sensor (2324), input device (2328), communication device (2330), and optional illumination source (2332).

Display

Patient data and physiological parameter predictions may be output on a display (e.g., display (2312)) of a computing device. In some variations, a display may include at least one of a light emitting diode (LED), liquid crystal display (LCD), electroluminescent display (ELD), plasma display panel (PDP), thin film transistor (TFT), organic light emitting diodes (OLED), electronic paper/e-ink display, laser display, and/or holographic display.

Processor

The processor (e.g., processor (2314)) described here may process data and/or other signals to control one or more components of the computing device. The processor may be configured to receive, process, compile, compute, predict, store, access, read, write, and/or transmit data and/or other signals. Additionally, or alternatively, the processor may be configured to control one or more components of a device and/or one or more components of computing device (e.g., laptop, tablet, personal computer).

In some variations, the processor may be configured to access or receive patient data, machine learning model training model set, and/or sensor signals from one or more of a computing device, and a storage medium (e.g., memory, flash drive, memory card). In some variations, the processor may be any suitable processing device configured to run and/or execute a set of instructions or code and may include one or more data processors, image processors, graphics processing units (GPU), physics processing units, digital signal processors (DSP), analog signal processors, mixed-signal processors, machine learning processors, deep learning processors, finite state machines (FSM), compression processors (e.g., data compression to reduce data rate and/or memory requirements), encryption processors (e.g., for secure wireless data transfer), and/or central processing units (CPU). The processor may be, for example, a general purpose processor, Field Programmable Gate Array (FPGA), an Application Specific Integrated Circuit (ASIC), a processor board, and/or the like. The processor may be configured to run and/or execute application processes and/or other modules, processes and/or functions associated with the system. The underlying device technologies may be provided in a variety of component types (e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and the like.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including C, C++, Java®, Python, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

Memory

The computing devices described here may include a memory (e.g., memory (2316)) configured to store data and/or information. In some variations, the memory may include one or more of a random access memory (RAM), static RAM (SRAM), dynamic RAM (DRAM), a memory buffer, an erasable programmable read-only memory (EPROM), an electrically erasable read-only memory (EEPROM), a read-only memory (ROM), flash memory, volatile memory, non-volatile memory, combinations thereof, and the like. In some variations, the memory may store instructions to cause the processor to execute modules, processes, and/or functions associated with the device, such as image processing, image display, data and/or signal transmission, data and/or signal reception, and/or communication. Some variations described herein may relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes.

In some variations, the memory may be configured to store any received data and/or data generated by the device. In some variations, the device may be configured to store graph data (e.g., second graph data nodes, user graph data, user activity, user preferences, and user input. In some variations, the memory may be configured to store data temporarily or permanently.

Optical Sensor

In some variations, an optical sensor may comprise one or more of a camera, photodetector, a photodiode, charged coupled device (CCD) or complementary metal-oxide semiconductor (CMOS) optical sensor, and an optical lens assembly. In some embodiments, the optical sensor may be configured to generate an image signal having a resolution of at least about 640 by 360 pixels and at least about 24 frames per second video.

In some variations, an illumination source may include one or more of a light emitter and/or an optical waveguide.

Non-limiting examples of a light emitter include incandescent, electric discharge (e.g., excimer lamp, fluorescent lamp, electrical gas-discharge lamp, plasma lamp, etc.), electroluminescence (e.g., light-emitting diodes, organic light-emitting diodes, laser, etc.), induction lighting, and fiber optics.

Input Device

In some variations, the display may include and/or be operatively coupled to an input device (2328) (e.g., touch screen) configured to receive input data from a user. For example, user input to an input device (2328) (e.g., keyboard, buttons, touch screen) may be received and processed by a processor (e.g., processor (2314)) and memory (e.g., memory (2316)) of the visualization system. The input device may include at least one switch configured to generate a user input. For example, an input device may include a touch surface for a user to provide input (e.g., finger contact to the touch surface) corresponding to a user input. An input device including a touch surface may be configured to detect contact and movement on the touch surface using any of a plurality of touch sensitivity technologies including capacitive, resistive, infrared, optical imaging, dispersive signal, acoustic pulse recognition, and surface acoustic wave technologies. In variations of an input device including at least one switch, a switch may have, for example, at least one of a button (e.g., hard key, soft key), touch surface, keyboard, analog stick (e.g., joystick), directional pad, mouse, trackball, jog dial, step switch, rocker switch, pointer device (e.g., stylus), motion sensor, image sensor, and microphone. A motion sensor may receive user movement data from an optical sensor and classify a user gesture as a user input. An audio sensor 2322 such as a microphone may receive audio data and recognize a user voice as a user input.

In some variations, the computing system may optionally include one more output devices in addition to the display, such as, for example, an audio device and haptic device. An audio device may audibly output any system data, alarms, and/or notifications. For example, the audio device may output an audible alarm when a malfunction is detected. In some variations, an audio device may include at least one of a speaker, piezoelectric audio device, magnetostrictive speaker, and/or digital speaker. In some variations, a user may communicate with other users using the audio device and a communication channel. For example, a user may form an audio communication channel (e.g., VoIP call).

Additionally or alternatively, the system may include a haptic device configured to provide additional sensory output (e.g., force feedback) to the user. For example, a haptic device may generate a tactile response (e.g., vibration) to confirm user input to an input device (2328) (e.g., touch surface). As another example, haptic feedback may notify that user input is overridden by the processor.

Communication Device

In some variations, the computing device may include a communication device (e.g., communication device (2330)) configured to communicate with another computing device and one or more databases. The communication device may be configured to connect the computing device to another system (e.g., Internet, remote server, graph database, media database) by wired or wireless connection. In some variations, the system may be in communication with other devices via one or more wired and/or wireless networks. In some variations, the communication device may include a radiofrequency receiver, transmitter, and/or optical (e.g., infrared) receiver and transmitter configured to communicate with one or more devices and/or networks. The communication device may communicate by wires and/or wirelessly.

The communication device may include RF circuitry configured to receive and send RF signals. The RF circuitry may convert electrical signals to/from electromagnetic signals and communicate with communications networks and other communications devices via the electromagnetic signals. The RF circuitry may include well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth.

Wireless communication through any of the devices may use any of plurality of communication standards, protocols and technologies, including but not limited to, Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (WiFi) (e.g., IEEE 802.11a, IEEE 802.11b, IEEE 802.11g, IEEE 802.11n, and the like), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol. In some variations, the devices herein may directly communicate with each other without transmitting data through a network (e.g., through NFC, Bluetooth, WiFi, RFID, and the like).

In some variations, the systems, devices, and methods described herein may be in communication with other wireless devices via, for example, one or more networks, each of which may be any type of network (e.g., wired network, wireless network). The communication may or may not be encrypted. A wireless network may refer to any type of digital network that is not connected by cables of any kind. Examples of wireless communication in a wireless network include, but are not limited to cellular, radio, satellite, and microwave communication. However, a wireless network may connect to a wired network in order to interface with the Internet, other carrier voice and data networks, business networks, and personal networks. A wired network is typically carried over copper twisted pair, coaxial cable and/or fiber optic cables. There are many different types of wired networks including wide area networks (WAN), metropolitan area networks (MAN), local area networks (LAN), Internet area networks (IAN), campus area networks (CAN), global area networks (GAN), like the Internet, and virtual private networks (VPN). Hereinafter, network refers to any combination of wireless, wired, public and private data networks that are typically interconnected through the Internet, to provide a unified networking and information access system.

Cellular communication may encompass technologies such as GSM, PCS, CDMA or GPRS, W-CDMA, EDGE or CDMA2000, LTE, WiMAX, and 5G networking standards. Some wireless network deployments combine networks from multiple cellular networks or use a mix of cellular, Wi-Fi, and satellite communication.

In some variations, a system may comprise an optical sensor configured to generate one or more image signals corresponding to a skin of the patient, a memory, a processor operatively coupled to the memory and the optical sensor. The processor may be configured to receive one or more image signals corresponding to a skin of the patient using the optical sensor, process the one or more image signals using a first machine learning model, and predict a physiological parameter based on the processed one or more image signals using a second machine learning model.

In some variations, a pressure sensor may be configured to measure finger pressure against the optical sensor. In some variations, an audio sensor may be configured to measure patient audio. In some variations, the system may comprise a handheld housing. Processing the one or more image signals and predicting the physiological parameter may be performed within the handheld housing. In some variations, a communication device and a display may be operatively coupled to the processor. The processor may be configured to establish a video conference using the communication device, and output the predicted physiological parameter using the display during the video conference. In some variations, a communication device may be operatively coupled to the processor. The processor may be configured to transmit the predicted physiological parameter to a predetermined device using the communication device.

While various inventive variations have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments/variations described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive variations described herein. It is, therefore, to be understood that the foregoing variations are presented by way of example only and that, within the scope of the appended claims and equivalents thereto, inventive variations may be practiced otherwise than as specifically described and claimed. Inventive variations of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The invention claimed is:

1. A method of monitoring a patient, comprising: at one or more processors: receiving one or more image signals corresponding to a skin of the patient; processing the one or more image signals using a first machine learning model; and predicting a physiological parameter comprising a blood pressure based on the processed one or more image signals using a second machine learning model and by calculating one or more of a short time Fourier transform (STFT), a continuous wavelet transform (CWT), a synchro-squeezing transform (SSQ), and a PPGlet of the processed one or more image signals as input to the second machine learning model, wherein predicting the physiological parameter comprises calculating for the processed one or more image signals one or more of systolic amplitude, pulse area, pulse interval, heart rate, time between systolic peak and end of a cardiac cycle, ratio of time before and after a systolic peak in a cardiac cycle, pulse width, maximum upslope, absorbance, Kaiser-Teager energy, signal energy, magnitude, phase, crest time, pulse interval, pulse width at half height (PWHH), Dicrotic Notch time ($T^{\sim}$), A2 time (A2T), diastolic time (DT), first derivative peak time (FDPT), pulse area (PA), area 1, area 2, pulse height (PH), ratio of b peak to a peak of a second derivative (b/a), ratio of e peak to a peak of the second derivative (e/a), modified Normalized Pulse Volume (mNPV), mean arterial pressure (MAP), cardiac output (CO), and total peripheral resistance (TPR).

2. A method of monitoring a patient, comprising: at one or more processors: receiving one or more image signals corresponding to a finger of the patient; selecting one or more spatial and temporal portions of the one or more image signals based on contact pressure of the finger to an optical sensor; and predicting a physiological parameter comprising a blood pressure based on the selected one or more spatial and temporal portions using a machine learning model and by calculating one or more of a short time Fourier transform (STFT), a continuous wavelet transform (CWT), a synchro-squeezing transform (SSQ), and a PPGlet of the one or more image signals as input to the machine learning model, wherein predicting the physiological parameter comprises calculating for the processed one or more image signals one or more of systolic amplitude, pulse area, pulse interval, heart rate, time between systolic peak and end of a cardiac cycle, ratio of time before and after a systolic peak in a cardiac cycle, pulse width, maximum upslope, absorbance, Kaiser-Teager energy, signal energy, magnitude, phase, crest time, pulse interval, pulse width at half height (PWHH), Dicrotic Notch time (Tn), A2 time (A2T), diastolic time (DT), first derivative peak time (FDPT), pulse area (PA), area 1, area 2, pulse height (PH), ratio of b peak to a peak of a second derivative (b/a), ratio of e peak to a peak of the second derivative (e/a), modified Normalized Pulse Volume (mNPV), mean arterial pressure (MAP), cardiac output (CO), and total peripheral resistance (TPR).

3. A method of monitoring a patient, comprising: at one or more processors: receiving one or more image signals corresponding to a face of the patient; processing the one or more image signals based on a shutter speed and signal gain of an optical sensor associated with the one or more image signals; and predicting a physiological parameter comprising a blood pressure based on the processed one or more image signals using a machine learning model and by calculating one or more of a short time Fourier transform (STFT), a continuous wavelet transform (CWT), a synchro-squeezing transform (SSQ), and a PPGlet of the processed one or more image signals as input to the machine learning model, wherein predicting the physiological parameter comprises calculating for the processed one or more image signals one or more of systolic amplitude, pulse area, pulse interval, heart rate, time between systolic peak and end of a cardiac cycle, ratio of time before and after a systolic peak in a cardiac cycle, pulse width, maximum upslope, absorbance, Kaiser-Teager energy, signal energy, magnitude, phase, crest time, pulse interval, pulse width at half height (PWHH), Dicrotic Notch time (Tn), A2 time (A2T), diastolic time (DT), first derivative peak time (FDPT), pulse area (PA), area 1, area 2, pulse height (PH), ratio of b peak to a peak of a second derivative (b/a), ratio of e peak to a peak of the second derivative (e/a), modified Normalized Pulse Volume (mNPV), mean arterial pressure (MAP), cardiac output (CO), and total peripheral resistance (TPR).

4. A method of monitoring a patient, comprising: at one or more processors: receiving one or more image signals corresponding to a finger and face of the patient; processing the one or more image signals using a first machine learning model; and predicting blood pressure based on the processed one or more image signals using a second machine learning model and by calculating one or more of a short time Fourier transform (STFT), a continuous wavelet transform (CWT), a synchro-squeezing transform (SSQ), and a PPGlet of the processed one or more image signals as input to the second machine learning model wherein predicting the physiological parameter comprises calculating for the processed one or more image signals one or more of systolic amplitude, pulse area, pulse interval, heart rate, time between systolic peak and end of a cardiac cycle, ratio of time before and after a systolic peak in a cardiac cycle, pulse width, maximum upslope, absorbance, Kaiser-Teager energy, signal energy, magnitude, phase, crest time, pulse interval, pulse width at half height (PWHH), Dicrotic Notch time (Tn), A2 time (A2T), diastolic time (DT), first derivative peak time (FDPT), pulse area (PA), area 1, area 2, pulse height (PH), ratio of b peak to a peak of a second derivative (b/a), ratio of e peak to a peak of the second derivative (e/a), modified Normalized Pulse Volume (mNPV), mean arterial pressure (MAP), cardiac output (CO), and total peripheral resistance (TPR).

5. The method of claim 1, wherein the skin corresponds to one or more of a finger and a face of the patient.

6. The method of claim 1, wherein the one or more image signals are generated by an optical sensor.

7. The method of claim 1, wherein the one or more image signals comprise a video.

8. The method of claim 1, wherein processing the one or more image signals selects one or more spatial and temporal portions of the one or more image signals.

9. The method of claim 1, wherein the first machine learning model is trained using a first machine learning model training set of photoplethysmography (PPG) signals based on a set of physiological parameter values.

10. The method of claim 9, wherein the set of predetermined physiological parameter values corresponds to one or more of heart rate, heart rate variability, oxygen saturation, respiratory rate, and blood pressure.

11. The method of claim 9, wherein the first machine learning model training set comprises PPG signals of a plurality of patients.

12. The method of claim 9, wherein the first machine learning model training set comprises artificial photoplethysmography PPG signals comprising a set of predetermined physiological parameter values.

13. The method of claim 9, wherein the first machine learning model training set comprises artificial noise comprising one or more of Gaussian noise, white noise, stretching, sloping, saturation, replacement, scaling, and baseline wander.

14. The method of claim 1, wherein processing the one or more image signals to select one or more portions of the one or more image signals is based on one or more of a dominant frequency, maximal variation, a correlation coefficient, contact pressure of a finger to an optical sensor, a cross-correlation among a set of cardiac cycles within a predetermined time period, cycle-by-cycle validation, bandpass filtering, smoothness, motion artifact removal, session filtering, and power spectrum.

15. The method of claim 1, wherein processing the one or more image signals comprises modifying the one or more image signals based on a shutter speed and signal gain of an optical sensor associated with the one or more image signals.

16. The method of claim 1, wherein processing the one or more image signals comprises generating one or more albedo signals corresponding to the one or more image signals.

17. The method of claim 16, wherein the one or more albedo signals comprises diffuse reflection and is absent specular reflection.

18. The method of claim 1, wherein processing the one or more image signals comprises: selecting a face and a neck of the skin of the one or more image signals; extracting a mean RGB signal of the selected skin as input to the first machine learning model.

19. The method of claim 18, wherein extracting the mean RGB signal comprises applying z-normalization separately to a plurality of sliding windows of the mean RGB signal, wherein the z-normalization comprises per temporal point normalization with respect to a local neighborhood.

20. The method of claim 19, wherein the first machine learning model training set is trained with a self-supervised learning mean RGB training set comprising artificial noise comprising one or more of Gaussian noise, Gaussian blur, cropping, and cutout.

21. The method of claim 1, wherein the first machine learning model comprises one or more of a residual neural network (ResNet), U-Net, variational autoencoder, denoising autoencoder neural network, autoencoder neural network with residual connections, vector quantized autoencoder, graph convolutional network, graph attention network, multi-head attention transformer, U-Net model, and combinations thereof.

22. The method of claim 1, wherein the first and second machine learning models comprise one or more of self-supervised learning, semi-supervised learning, weakly-supervised learning, and federated learning.

23. The method of claim 1, wherein processing the one or more image signals comprises generating a polygon mesh corresponding to a face and neck of the patient.

24. The method of claim 1, wherein processing the one or more image signals comprises generating a virtual multispectral PPG signal.

25. The method of claim 1, wherein processing the one or more image signals comprises applying one or more of a Kalman filter, principal component analysis, independent component analysis, and blind source separation.

26. The method of claim 1, wherein the physiological parameter further comprises one or more of oxygen saturation and blood glucose.

27. The method of claim 26, wherein the second machine learning model comprises one or more of a long short-term memory network (LSTM), a bi-directional long short-term memory network (bi-LSTM), convolutional neural network (CNN), deep neural network, a gradient boosting model, transformers, and combinations thereof.

28. The method of claim 1, wherein the second machine learning model comprises one or more of a Bayesian network, a long short-term memory network (LSTM), a bi-directional long short-term memory network (bi-LSTM), a convolutional neural network (CNN), a random forest, a gradient boosting model, a Wave net model, a residual neural network (ResNet) model, a WaveResNet model, a support vector machine (SVM), autoencoder, and combinations thereof.

29. The method of claim 1, wherein predicting the physiological parameter comprises calculating for the processed one or more image signals one or more of systolic amplitude, pulse area, pulse interval, heart rate, time between systolic peak and end of a cardiac cycle, ratio of time before and after a systolic peak in a cardiac cycle, pulse width, maximum upslope, absorbance, Kaiser-Teager energy, signal energy, magnitude, phase, crest time, pulse interval, pulse width at half height (PWHH), Dicrotic Notch time (Tn), A2 time (A2T), diastolic time (DT), first derivative peak time (FDPT), pulse area (PA), area 1, area 2, pulse height (PH), ratio of b peak to a peak of a second derivative (b/a), ratio of e peak to a peak of the second derivative (e/a), modified Normalized Pulse Volume (mNPV), mean arterial pressure (MAP), cardiac output (CO), and total peripheral resistance (TPR).

30. The method of claim 1, wherein the blood pressure comprises a continuous arterial blood pressure.

31. The method of claim 30, wherein predicting the physiological parameter comprises calculating for the processed one or more image signals an upper envelope corresponding to systolic blood pressure and a lower envelope corresponding to diastolic blood pressure.

32. The method of claim 4, wherein predicting the blood pressure comprises calculating for the processed one or more image signals one or more of a pulse transit time (PTT) based on a plurality of portions of the face of the patient, a PTT between the face and the finger, and a modified Normalized Pulse Volume (mNPV) and a photoplethysmography (PPG) signal based on the finger or the face.

33. The method of claim 1, wherein the physiological parameter further comprises respiratory rate.

34. The method of claim 33, wherein predicting the physiological parameter comprises cropping a respiratory rate frequency region.

35. The method of claim 1, wherein the second machine learning model comprises a U-Net neural network.

36. The method of claim 26, wherein processing the one or more image signals comprises extracting one or more of frequency modulation, amplitude modulation, and baseline wander of one or more color channels of the PPG signal.

37. The method of claim 1, wherein the physiological parameter further comprises heart rate.

38. The method of claim 37, wherein predicting the physiological parameter comprises one or more of cropping a heart rate frequency region, beat detection, peak detection, and combinations thereof.

39. The method of claim 1, wherein the physiological parameter further comprises heart rate variability.

40. The method of claim 39, wherein the heart rate variability comprises one or more of a standard deviation of NN intervals (SDNN), a mean of the NN (e.g., peak-to-peak distance) intervals, and a root mean square of successive differences between normal heartbeats (RMSSD).

41. The method of claim 39, wherein predicting the physiological parameter comprises extracting color channels from the processed one or more image signals and identifying a set of peak locations.

42. A system, comprising: an optical sensor configured to generate one or more image signals corresponding to a skin of the patient; a memory; and a processor operatively coupled to the memory and the optical sensor, the processor configured to: receive one or more image signals corresponding to a skin of the patient using the optical sensor; process the one or more image signals using a first machine learning model; predict a physiological parameter comprising a blood pressure based on the processed one or more image signals using a second machine learning model; and calculate one or more of a short time Fourier transform (STFT), a continuous wavelet transform (CWT), a synchrosqueezing transform (SSQ), and a PPGlet of the processed one or more image signals as input to the second machine learning model as part of the physiological parameter prediction, wherein predicting the physiological parameter comprises calculating for the processed one or more image signals one or more of systolic amplitude, pulse area, pulse interval, heart rate, time between systolic peak and end of a cardiac cycle, ratio of time before and after a systolic peak in a cardiac cycle, pulse width, maximum upslope, absorbance, Kaiser-Teager energy, signal energy, magnitude, phase, crest time, pulse interval, pulse width at half height (PWHH), Dicrotic Notch time (Tn), A2 time (A2T), diastolic time (DT), first derivative peak time (FDPT), pulse area (PA), area 1, area 2, pulse height (PH), ratio of b peak to a peak of a second derivative (b/a), ratio of e peak to a peak of the second derivative (e/a), modified Normalized Pulse Volume (mNPV), mean arterial pressure (MAP), cardiac output (CO), and total peripheral resistance (TPR).

43. The system of claim 42, comprising a pressure sensor configured to measure finger pressure against the optical sensor.

44. The system of claim 42, comprising an audio sensor configured to measure patient audio.

45. The system of claim 42, comprising a handheld housing, wherein processing the one or more image signals and predicting the physiological parameter is performed within the handheld housing.

46. The system of claim 42, further comprising a communication device and a display operatively coupled to the processor, the processor configured to: establish a video conference using the communication device; and output the predicted physiological parameter using the display during the video conference.

47. The system of claim 42, further comprising a communication device operatively coupled to the processor, the processor configured to: transmit the predicted physiological parameter to a predetermined device using the communication device.

* * * * *